(12) United States Patent
Seo et al.

(10) Patent No.: US 7,041,390 B2
(45) Date of Patent: May 9, 2006

(54) ORGANOMETAL COMPLEX, ELECTROLUMINESCENCE MATERIAL USING THE COMPLEX, AND ELECTROLUMINESCENCE ELEMENT USING THE COMPLEX

(75) Inventors: Satoshi Seo, Kanagawa (JP); Hideko Inoue, Kanagawa (JP); Atsushi Tokuda, Kanagawa (JP)

(73) Assignee: Semiconductor Energy Laboratory Co., Ltd., (JP)

( * ) Notice: Subject to any disclaimer, the term of this patent is extended or adjusted under 35 U.S.C. 154(b) by 0 days.

(21) Appl. No.: 10/777,519

(22) Filed: Feb. 12, 2004

(65) Prior Publication Data
US 2005/0006625 A1    Jan. 13, 2005

(30) Foreign Application Priority Data

Feb. 14, 2003 (JP) .............................. 2003-035969
Jun. 30, 2003 (JP) .............................. 2003-188960

(51) Int. Cl.
C09K 11/06 (2006.01)
H05B 33/14 (2006.01)

(52) U.S. Cl. ..................... 428/690; 428/917; 313/504; 252/301.16; 544/4; 544/64; 546/4; 546/5; 546/10; 548/403

(58) Field of Classification Search .............. 428/690, 428/917; 313/504, 506; 252/301.16; 257/40; 544/4, 38, 64, 102; 546/4, 5, 7, 10; 548/403
See application file for complete search history.

(56) References Cited

U.S. PATENT DOCUMENTS

| 6,097,147 | A | 8/2000 | Baldo et al. ................ 313/506 |
| 2002/0034656 | A1 | 3/2002 | Thompson et al. ......... 428/690 |
| 2002/0064681 | A1 | 5/2002 | Takiguchi et al. .......... 428/690 |
| 2003/0017361 | A1 | 1/2003 | Thompson et al. ......... 428/690 |

FOREIGN PATENT DOCUMENTS

EP    1 191 613 A2    3/2002
JP    2003-342284    12/2003

OTHER PUBLICATIONS

International Search Report for appl. No. PCT/JP2004/001165, mailed Apr. 27, 2004 (In Japanese).

Written opinion re appl. No. PCT/JP2004/001165, dated Apr. 27, 2004, (with partial English translation).

Tsutsui, T., "The Operation Mechanism and the Light Emission Efficiency of the Organic EL Element," Textbook of the $3^{rd}$ Seminar at Division of Organic Molecular Electronics and Bioelectronics, The Japan Society of Applied Physics, pp. 31-37; with English translation pp. 1-11, (1993).

Inoue, H. et al, "A Reaction of Singlet Oxygen with an Unsaturated Organic Molecule," 6.1.4, Quencher and Photosensitizer, *Basic Chemistry Course PHOTOCHEMISTRY I*, pp. 106-110, Maruzen Co. publisher, Japan (1999).

O'Brien, D.F. et al, "Improved Energy Transfer in Electrophosphorescent Devices," Applied Physics Letters, vol. 74, No. 3, pp. 442-444, Jan. 18, (1999).

Tsutsui, T. et al, "High Quantum Efficiency in Organic Light-Emitting Devices with Iridium-Complex as a Triplet Emissive Center," Japanese Journal of Applied Physics, vol. 38, part 2, No. 12B, pp. L1502-L1504, Dec. 15, (1999).

Baldo, M.A. et al, "High-Efficiency Fluorescent Organic Light-Emitting Devices Using a Phosphorescent Sensitizer," Nature, vol. 403, pp. 750-753, Feb. 17 (2000).

Thompson, M.E. et al, "Phosphorescent Materials and Devices," The $10^{th}$ International Workshop on Inorganic and Organic Electroluminescence, EL '00, pp. 35-38, (2000).

*Primary Examiner*—Marie Yamnitzky
(74) *Attorney, Agent, or Firm*—Cook, Alex, McFarron, Manzo, Cummings & Mehler, Ltd.

(57) ABSTRACT

Organometal complexes which are obtainable with a good yield by using a ligand which can be easily synthesized are provided. The organometal complexes are excellent in heat resistance. An electroluminescence element having high light emission efficiency is manufactured using the organometal complex. Therefore, the organometal complex represented by the general formula (1) is synthesized. Further, this is applied to the electroluminescence element.

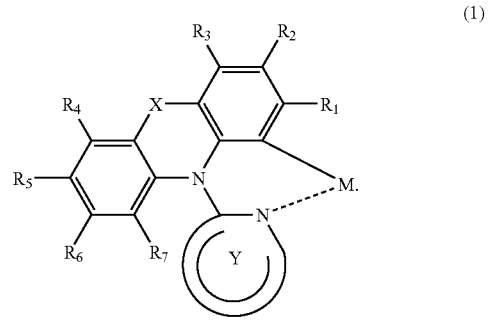

(1)

29 Claims, 8 Drawing Sheets

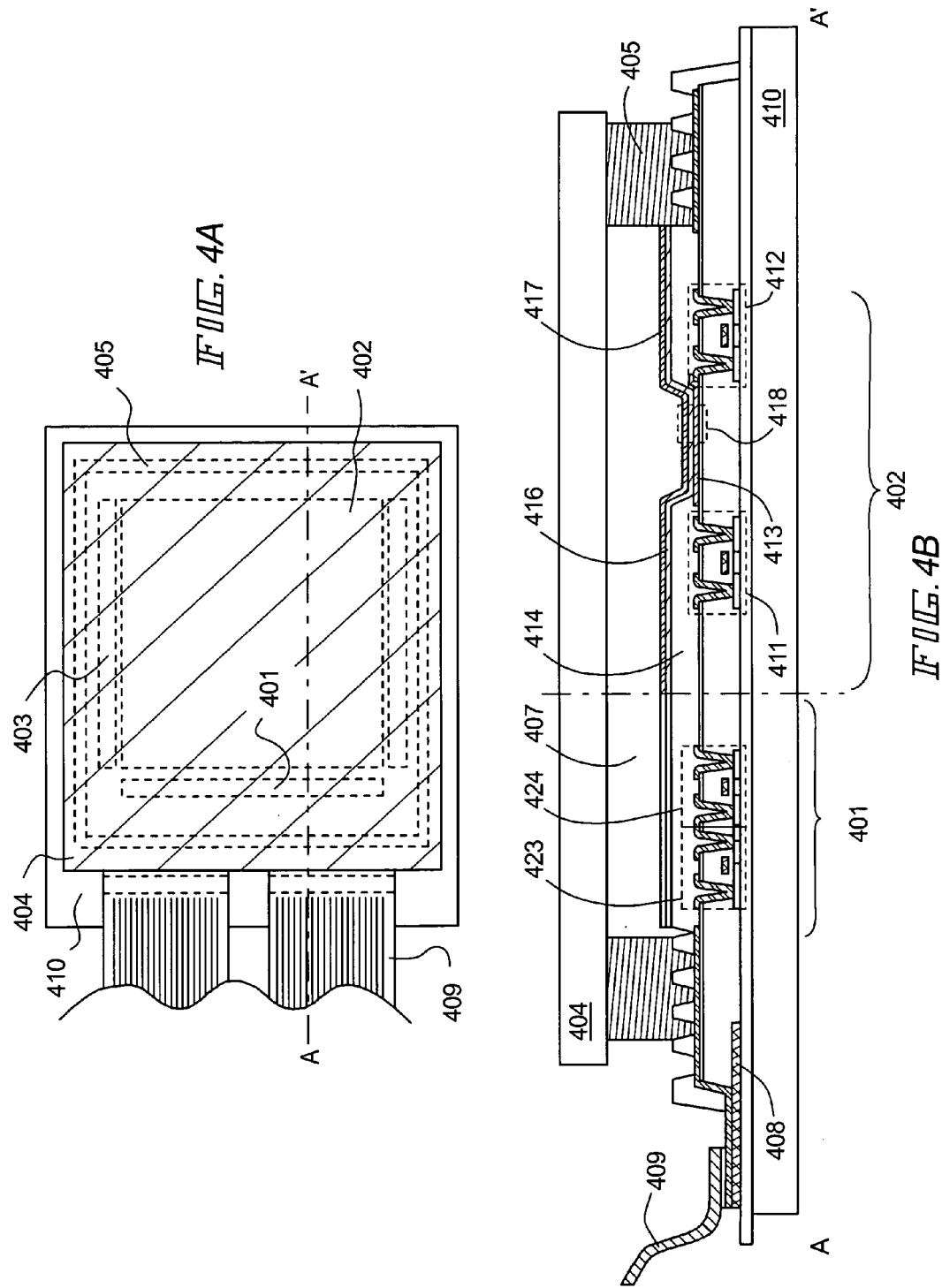

ORGANOMETAL COMPLEX, ELECTROLUMINESCENCE MATERIAL USING THE COMPLEX, AND ELECTROLUMINESCENCE ELEMENT USING THE COMPLEX

TECHNICAL FIELD

The present invention relates to novel organometal complexes. Particularly, this invention relates to the organometal complexes each of which is capable of converting a triplet excitation state into light emission. Also, this invention relates to an electroluminescence material using the organometal complex. Further, this invention relates to an electroluminescence element which has an anode, a cathode, and a layer (hereinafter referred to as electroluminescence layer) containing an organic compound capable of achieving light emission upon application of electric field and is formed by using the organometal complex.

BACKGROUND OF THE INVENTION

Organic compounds (organic molecules) are brought into a state having energy (excitation state) by absorbing light. By going through this excitation state, various reactions (photochemical reactions) are caused in some cases, while luminescence is generated in other cases; therefore, the organic compounds have found various applications.

As one example of the photochemical reactions, a reaction (oxygenation) between singlet oxygen and an unsaturated organic molecule is known (see Non-Patent Document 1, for example). Since a ground state of an oxygen molecule is a triplet state, the oxygen in singlet state (singlet oxygen) is not generated by a direct photoexcitation. However, under the presence of another triplet excitation molecule, the singlet oxygen is generated to achieve the oxygenation reaction. In this case, a compound capable of forming the triplet excitation molecule is referred to as a photosensitizer.

(Non-Patent Document 1) Haruo Inoue and three others, Basic Chemical Course Photochemistry I (Maruzen Co., Ltd.), 106–110

As described above, in order to generate the singlet oxygen, the photosensitizer capable of forming the triplet excitation molecule with the photoexcitation is necessary. However, since the ground state of ordinary organic compounds is a singlet state, the photoexcitation to the triplet excitation state results in a forbidden transition, and the triplet excitation molecule is hardly generated (a singlet excitation molecule is ordinarily generated). Therefore, as such photosensitizer, a compound which readily causes intersystem crossing from the singlet excitation state to the triplet excitation state (or a compound allowing the forbidden transition which the photoexcitation directly leads to the triplet excitation state) is in demand. In other words, such compound can be used as the photosensitizer and is useful.

Also, such compounds usually discharge phosphorescence. The phosphorescence is light emission caused by a transition between energies different in multiplicity and, in terms of ordinary organic compounds, means light emission caused when the triplet excitation state returns to the singlet ground state (in contrast, the light emission caused when the singlet excitation state returns to the singlet ground state is called fluorescence). One example of applicable fields of the compound capable of discharging the phosphorescence, i.e. the compound capable of converting the triplet excitation state into light emission (hereinafter referred to as phosphorescent compound), is an electroluminescence element using the organic compound as a luminescent compound.

The electroluminescence element is a device attracting attention as a next generation flat panel display element thanks to its characteristics such as thin and lightweight, high speed response, and direct current low voltage driving. Also, because of its self-luminous and wide viewing angle, the element has a comparatively good visibility and is considered to be effective as an element to be used as a display screen of mobile appliances.

In the case of using the organic compound as an illuminant, a light emission mechanism of the electroluminescence element is a carrier injection type. That is, by applying a voltage to an electroluminescence layer being sandwiched between electrodes, electrons injected form a cathode are recombined with holes injected from an anode in the electroluminescence layer to form excited molecules which discharge energy to emit light when they return to the ground state.

Types of the excited molecules can be, as is the case with the photoexcitation described above, the singlet excitation state ($S^*$) and the triplet excitation state ($T^*$). Further, a statistical generation ratio of the excited molecules in the electroluminescence element is considered to be $S^*:T^*=1:3$ (see Non-Patent Document 2, for example).

(Non-Patent Document 2) Tetsuo Tsutsui, Society of Applied Physics, Text for the Third Training Class of Organic Molecules/Bioelectronics Special-interest Group, 31–37 (1993)

However, the light emission (phosphorescence) from the triplet excitation state of general organic compounds is not observed at a room temperature, and, ordinarily, only the light emission from the singlet excitation state (fluorescence) is observed. This is because the ground state of the organic compounds is, in general, the singlet ground state ($S_0$); therefore, $T^*$-$S_0$ transition (phosphorescence process) is a strong forbidden transition, and $S^*$-$S_0$ transition (fluorescence process) is an allowable transition.

Accordingly, a logical limit of internal quantum efficiency (a ratio of generated photons to injected carriers) in the electroluminescence element has been set to 25% based on the ratio of $S^*:T^*=1:3$.

But, since the $T^*$-$S_0$ transition (phosphorescence process) is allowed when the above-described phosphorescent compound is used, the internal quantum efficiency can logically be improved to 75 to 100%. That is, light emission efficiency of 3 to 4 times that of the conventional one can be achieved. Actually, electroluminescence elements using phosphorescent compounds have been proposed one after another, and high-level light emission efficiency thereof has been noted (see Non-Patent Documents 3 and 4, for example).

(Non-Patent Document 3) D. F. O'Brien and three others, Applied Physics Letters, vol. 74, No. 3, 442–444 (1999)

(Non-Patent Document 4) Tetsuo Tsutsui and eight others, Japanese Journal of Applied Physics, vol. 38, L1502–L1504 (1999)

A porphyrin complex whose central metal is platinum is used in Non-Patent Document 3, while an organometal complex whose central metal is iridium is used in Non-Patent Document 4, each of the complexes being the phosphorescent compound.

Further, by alternately stacking a layer containing the organometal complex whose central metal is iridium (hereinafter referred to as iridium complex) and a layer containing DCM2 which is a known fluorescent compound, it is possible to move triplet excitation energy generated by the iridium complex to DCM2 so as to cause the energy to contribute to light emission of DCM2 (see Non-Patent Document 5, for example). In this case, since the quantity of the singlet excitation state of DCM2 (25% or less under ordinary circumstances) is increased compared with the ordinary circumstances, the light emission efficiency of DCM2 increases. In other words, this means a sensitization effect of iridium complex which is a phosphorescent compound.

(Non-Patent Document 5) M. A. Baldo and two others, Nature (London), vol. 403, 750–753 (2000)

As proved by Non-Patent Documents 3 to 5, the electroluminescence element using phosphorescent compounds is capable of achieving the light emission efficiency higher than the conventional example (i.e. capable of achieving high luminosity with a small current). Therefore, it is considered that the electroluminescence element using phosphorescent compounds will assume a great importance in future developments as a measure for achieving high luminosity emission and high light emission efficiency.

The phosphorescent compounds are useful as the photosensitizer and also as a phosphorescent material for the electroluminescence element because they readily cause the intersystem crossing and readily produce light emission (phosphorescence) from the triplet excitation state as described above, and much hope is placed on the compounds; however, the number thereof is small under the present situation.

Among the small number of phosphorescent compounds, the iridium complex used in Non-Patent Documents 4 and 5 is called an orthometal complex which is a kind of the organometal complexes. Since this complex has a phosphorescence life of a several hundreds of nanoseconds and is high in phosphorescence quantum yield, a reduction in efficiency due to an increase in luminosity is smaller than that of the porphyrin complex, so that the complex is effectively used in the electroluminescence element. For this reason, such organometal complex is one of polestars for synthesizing a compound which readily causes the direct photoexcitation or the intersystem crossing to the triplet excitation state, or the phosphorescent compounds.

The iridium complex used in Non-Patent Documents 4 and 5 has a relatively simple ligand structure and exhibits a green light emission having a good color purity; however, it is necessary to change the ligand structure in order to change the light emission color to a different one. For example, in Non-Patent Document 6, various ligands and iridium complexes using the ligands are synthesized and several light emission colors are realized.

(Non-Patent Document 6) M. Thompson and ten others, Tenth International Workshop on Inorganic and Organic Electroluminescence (EL '00), 35–38

However, almost all of the ligands are limited to those capable of forming a five-membered ring with the central metal, and, under the current situation, a desired light emission color is selected among the ligands. That is to say, there is a problem that the number of usable ligands is still small.

Also, many of the ligands are difficult to synthesize or require a large number of steps for the synthesis, thereby leading to an increase in cost of the material itself. From the cost point of view, the yield of the organometal complex itself is also important.

Further, the organometal complex is generally subject to decomposition, and a decomposition temperature of the one which is less subject to decomposition is not high at all. Therefore, the poor heat resistance is problematic in the application thereof to an electronic device such as the electroluminescence element.

In view of the above, an organometal complex which is obtainable with a high yield by using a ligand which can be easily synthesized and excellent in heat resistance is in demand. By synthesizing such organometal complex, it is possible to obtain a photosensitizer and a phosphorescent material which are low in cost and high in heat resistance.

Therefore, in the present invention, it is intended to provide a novel organometal complex which is obtained with a high yield by using a ligand which can be easily synthesized. Particularly, it is intended to provide the novel organometal complex excellent in heat resistance.

Further, it is intended to provide an electroluminescence element which is high in light emission efficiency by manufacturing the electroluminescence element using the organometal complex. Further, it is intended to provide a light emission device which is low in power consumption by manufacturing the light emission device using the electroluminescence element.

SUMMARY OF THE INVENTION

The inventors of the present invention have conducted extensive researches to find that it is possible to synthesize an organometal complex which forms a six-membered ring with a central metal by subjecting a ligand represented by the following general formula (12) to a cyclometallation reaction with a central metal staple.

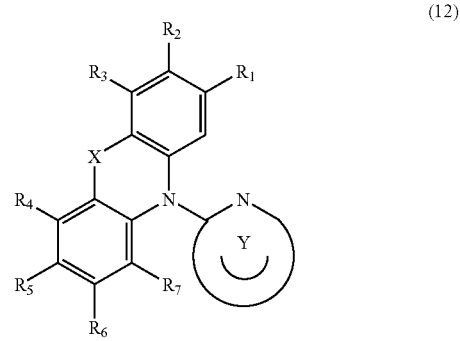

Therefore, a structure of this invention is to provide the organometal complex having a partial structure represented by the following general formula (1).

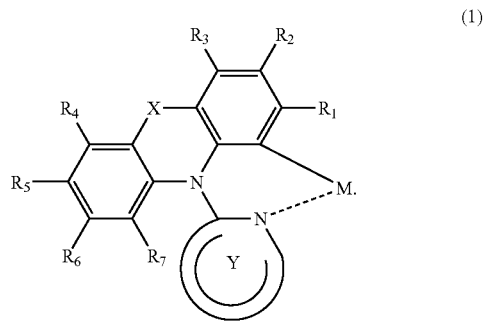

(R1 to R7 may be the same or different respectively and represent any one of a hydrogen atom, a halogen atom, a lower alkyl group, an alkoxy group, an acyl group, a nitro group, a cyano group, an amino group, a dialkylamino group, a diarylamino group, a vinyl group which may have a substituent, an aryl group which may have a substituent, or a heterocyclic residue which may have a substituent. Each of pairs of R1 and R2, R2 and R3, R4 and R5, and R5 and R6 may be combined into an aromatic ring. X represents an oxygen atom or a sulfur atom. Y represents a heterocyclic residue containing a nitrogen atom as a heteroatom. M represents a group IX atom or a group X atom.)

Another structure of this invention is to provide an organometal complex of the following general formula (2).

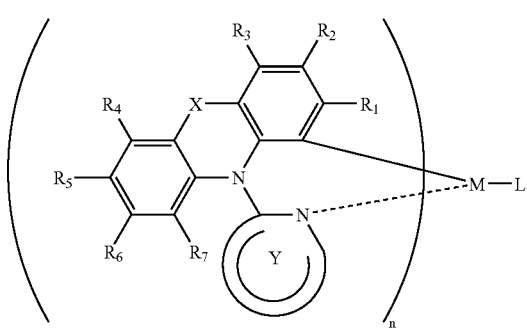

(2)

(R1 to R7 may be the same or different respectively and represent any one of a hydrogen atom, a halogen atom, a lower alkyl group, an alkoxy group, an acyl group, a nitro group, a cyano group, an amino group, a dialkylamino group, a diarylamino group, a vinyl group which may have a substituent, an aryl group which may have a substituent, or a heterocyclic residue which may have a substituent. Each of pairs of R1 and R2, R2 and R3, R4 and R5, and R5 and R6 may be combined into an aromatic ring. X represents an oxygen atom or a sulfur atom. Y represents a heterocyclic residue containing a nitrogen atom as a heteroatom. M represents a group IX atom or a group X atom, and n=2 when M is the group IX atom, while n=1 when M is the group X atom. L represents any one of a monoanionic bidentate chelate ligand having a beta-diketone structure, a monoanionic bidentate chelate ligand having a carboxyl group, or a monoanionic bidentate chelate ligand having a phenolic hydroxyl group.)

Since it is possible to synthesize the ligand represented by the general formula (12) remarkably easily, these organometal complexes are synthesized at an advantageously low cost. Also, a yield thereof is good.

It is preferable that the heterocyclic residue Y in the general formulas (1) and (2) may be a heterocyclic residue comprising a five-membered ring or a six-membered ring such as a 2-pyridyl group, a 2-oxazolyl group, and a 2-thiazolyl group from a steric point of view. Particularly preferred is 2-pyridyl because it is easily synthesized.

Also, a preferred structure of this invention is to provide an organometal complex having a partial structure represented by the following general formula (3).

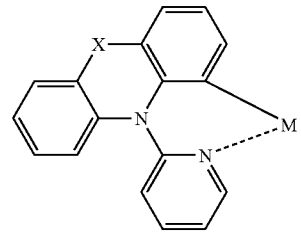

(3)

(wherein X represents an oxygen atom or a sulfur atom. M represents a group IX atom or a group X atom)

Further, a preferred structure of this invention is to provide an organometal complex represented by the following general formula (4).

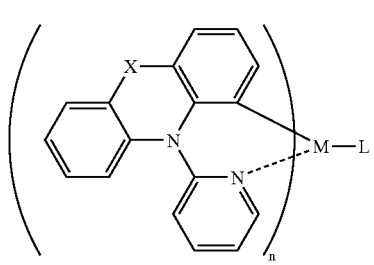

(4)

(wherein X represents an oxygen atom or a sulfur atom. M represents a group IX atom or a group X atom, and n=2 when M is the group IX atom, while n=1 when M is the group X atom. L represents any one of a monoanionic bidentate chelate ligand having a beta-diketone structure, a monoanionic bidentate chelate ligand having a carboxyl group, or a monoanionic bidentate chelate ligand having a phenolic hydroxyl group.)

Further, the inventors have found that the organometal complexes of this invention are capable of emitting phosphorescence. In order to achieve the phosphorescence more efficiently, it is preferable to use a heavy metal as the central metal from the point of view of a heavy atom effect. Therefore, this invention is characterized in that the central metal is an iridium atom or a platinum atom. Meanwhile, X may be preferably oxygen.

In the general formulas (2) or (4), though the ligand L is not limited so far as it is the monoanionic bidentate chelate ligand having a beta-diketone structure, the monoanionic bidentate chelate ligand having a carboxyl group, or the monoanionic bidentate chelate ligand having a phenolic hydroxyl group, it is preferable to use any one of monoanionic bidentate chelate ligands represented by the following structural formulas (5) to (11). These ligands are effective since they are high in coordination ability and obtainable at low cost.

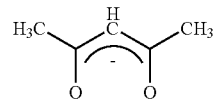

(5)

-continued

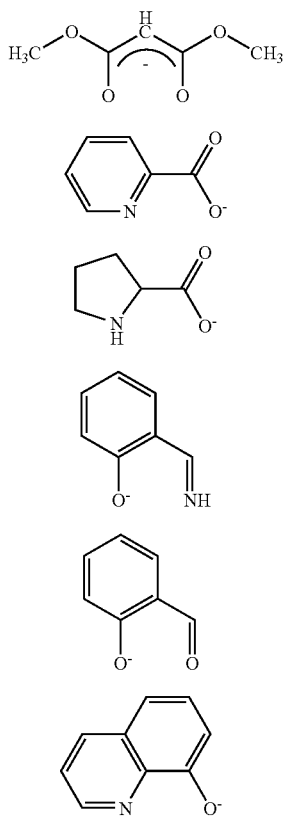

By the way, since the organometal complexes of this invention is capable of converting the triplet excitation state into light emission, it enables high efficiency of the electroluminescence element when applied to the electroluminescence element and is significantly effective. Therefore, the electroluminescence element using the organometal complex of this invention is also encompassed in this invention.

Though each of the organometal complexes of this invention may be used as the substance for causing sensitization as mentioned in Non-Patent Document 5 or a substance in a carrier transport layer such as a hole transport layer, a usage thereof as an illuminant is effective in view of the light emission efficiency. Therefore, this invention is characterized by the electroluminescence element using the organometal complex as an illuminant.

Since the electroluminescence element of this invention can realize high light emission efficiency, a light emission device using the electroluminescence element as a light emission element can realize low power consumption. Therefore, a light emission device using the electroluminescence element of this invention is also encompassed in this invention.

As used in this description, the light emission device means an image display device or a light emission device using the electroluminescence element as the light emission element. Further, the light emission device includes a module where a connector such as an anisotropic conductive film (FPC: Flexible Printed Circuit), a TAB (Tape Automated Bonding) tape, and a TCP (Tape Carrier Package) is attached to an electroluminescence element; a module where a printed wiring board is mounted at the tip of the TAB tape or the TCP; and a module where an IC (Integrated Circuit) is directly mounted on an electroluminescence element by COG (Chip On Glass) method.

BRIEF DESCRIPTION OF THE DRAWINGS

FIGS. 4A–4B are illustrations of light emission devices.

DETAILED DESCRIPTION OF THE PRESENTLY PREFERRED EMBODIMENTS

Figure 1:
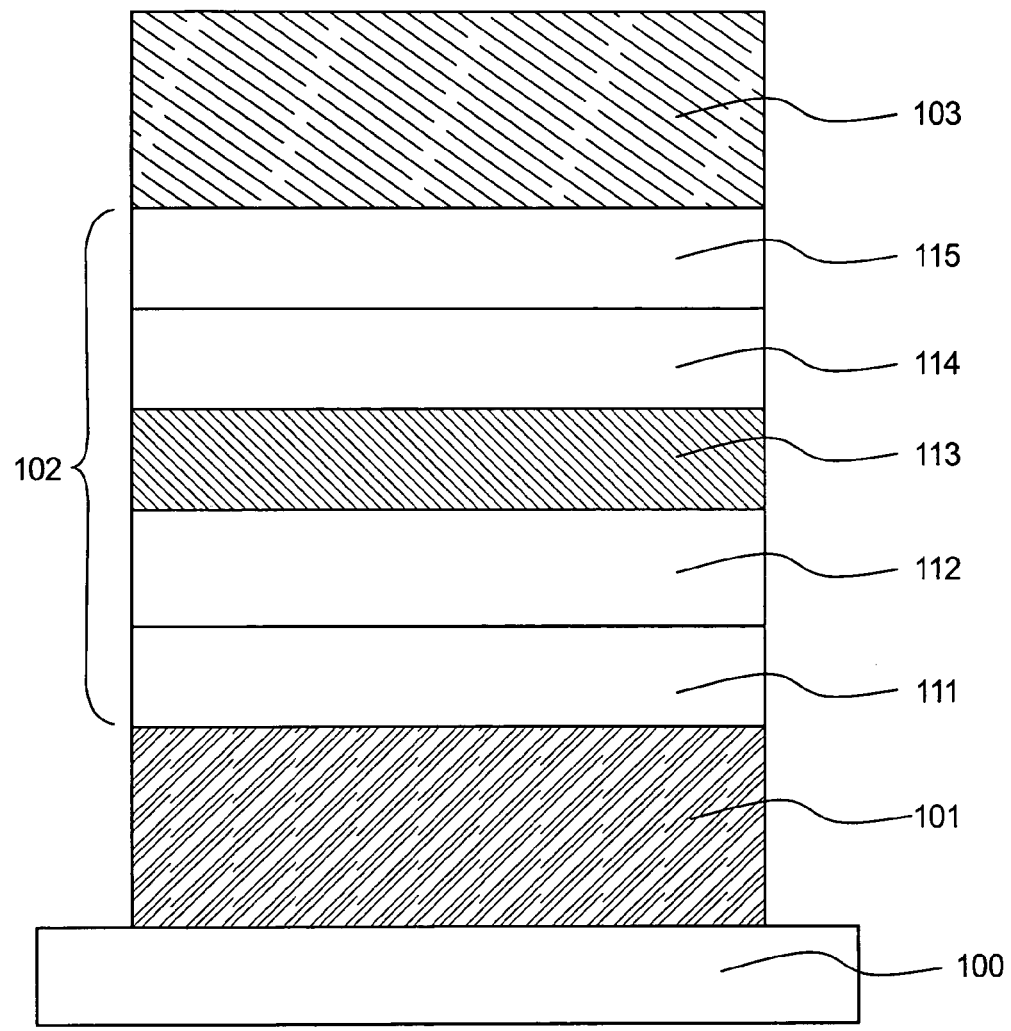
FIG. 1 is an illustration of an element structure of an electroluminescence element according to Embodiment Mode 1.

It is possible to synthesize a ligand represented by the following general formula (12) by, for example, the following synthesis scheme (a) where a phenothiazine derivative A is reacted with an iodinated substance B which is a heterocyclic compound. Note that the synthesis method is not limited to the above.

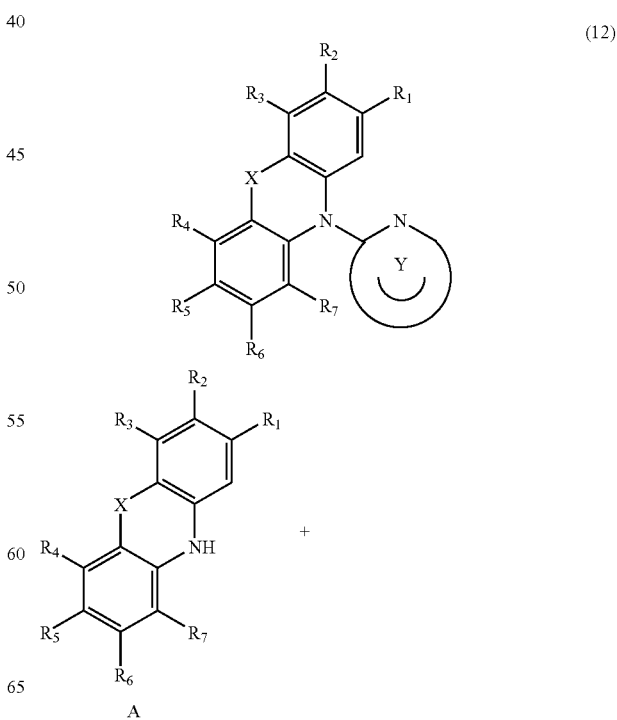

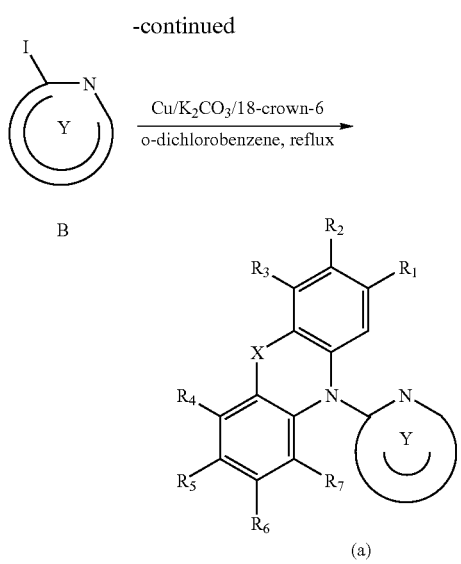

(a)

In the above general formula (12), R1 to R7 may be the same or different respectively and represent any one of a hydrogen atom, a halogen atom, a lower alkyl group, an alkoxy group, an acyl group, a nitro group, a cyano group, an amino group, a dialkylamino group, a diarylamino group, a vinyl group which may have a substituent, an aryl group which may have a substituent, or a heterocyclic residue which may have a substituent. Each of pairs of R1 and R2, R2 and R3, R4 and R5, and R5 and R6 may be combined into an aromatic ring.

In this case, usable as the lower alkyl group are a methyl group, an ethyl group, an n-propyl group, an isopropyl group, an n-butyl group, a sec-butyl group, a tert-butyl group, a hexyl group, and the like, and those having 1 to 6 carbon atoms may be preferably used. Further, a halogenated alkyl group such as a trifluoromethyl group or a cycloalkyl group such as a cyclohexyl group may be used. Usable as the alkoxy group are a methoxy group, an ethoxy group, an n-propoxy group, an isopropoxy group, an n-butoxy group, a sec-butoxy group, a tert-butoxy group, a hexoxy group, and the like, and those having 1 to 6 carbon atoms may be preferably used. Usable as the acyl group may be an acetyl group. Usable as the dialkylamino group are a dimethylamino group, a diethylamino group, and the like, and those having 1 to 4 carbon atoms in an alkyl chain may be preferably used. Usable as the diarylamino group are a diphenylamino group, a bis(α-naphthyl)amino group, and the like, and a substituted aryl amino group such as a bis(m-tolyl)amino group may be used. A vinyl group having a substituent such as a diphenylvinyl group may be used as the vinyl group. Usable as the aryl group may be a non-substituted aryl group such as a phenyl group and a naphthyl group and a substituted aryl group such as an o-tolyl group, m-tolyl group, p-tolyl group, a xylyl group, a methoxyphenyl group, an ethoxyphenyl group, and a fluorophenyl group. Examples of the heterocyclic residue are a pyridyl group, a furyl group, a thienyl group, and the like.

In the above general formula (12), X represents an oxygen atom or a sulfur atom. Though it is possible to use a polycyclic group such as a 2-benzooxazolyl group as the heterocyclic residue Y, it is preferable to use a heterocyclic residue of a five-membered ring or a six-membered ring in view of the steric structure which enables coordination without disturbing coordination to a metal. Specific examples of the heterocyclic residue are a 2-pyridyl group, a 4-pyridyl group, a 2-oxazolyl group, and a 2-thiazolyl group.

More specific examples of the ligand represented by the general formula (12) are 10-(2-pyridyl)phenothiazine, 10-(2-pyridyl)-3,7-dimethylphenothiazine, 10-(2-pyridyl)4,6-dimethylphenothiazine, 10-(2-pyridyl)-3,7-dimethoxyphenothiazine, 10-(2-pyridyl)-3,7-bis(dimethylamino) phenothiazine, 10-(2-pyridyl)-3,7-bis(diphenylamino) phenothiazine, 10-(2-pyridyl)-3,7-bis(diphenylvinyl) phenothiazine, 10-(2-pyridyl)-dibenzo[c] [h]-phenothiazine, 10-(2-oxazolyl)phenothiazine, 10-(2-thiazolyl)phenothiazine, 10-(2-pyridyl)phenoxazine, 10-(2-pyridyl)-3,7-dimethylphenoxazine, 10-(2-pyridyl)4,6-dimethylphenoxazine, 10-(2-pyridyl)-3,7-dimethoxyphenoxazine, 10-(2-pyridyl)-3,7-bis(dimethylamino)phenoxazine, 10-(2-pyridyl)-3,7-bis(diphenylamino)phenoxazine, 10-(2-pyridyl)-3,7-bis(diphenylvinyl)phenoxazine, 10-(2-pyridyl)dibenzo-[c] [h]-phenoxazine, 10-(2-oxazolyl)phenoxazine, 10-(2-thiazolyl) phenoxazine, and the like, and the ligand is not limited to the above in this invention.

Next, An organometal complex of this invention having a partial structure represented by the following general formula (1) is formed by using the above-described ligand (12). R1 to R7, X, and Y of the general formula (1) are the same as those of the general formula (12) of the above-described ligand. M represents a group IX atom or a group X atom, and specific examples thereof are a platinum atom or an iridium atom.

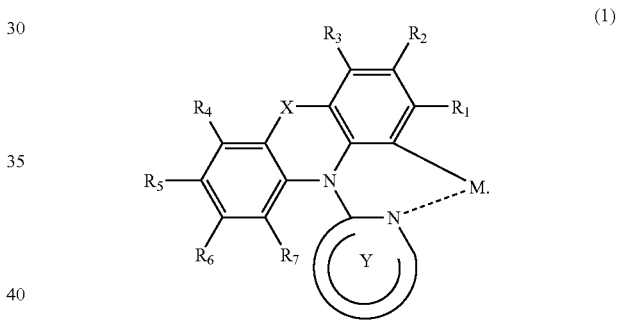

(1)

As one example of the formation of the organometal complex of this invention, a formation of an organometal complex represented by the following general formula (2) using a bidentate chelate ligand L will be described below. R1 to R7, X, and Y of the general formula (2) are the same as those of the general formula (12) of the above-described ligand. M represents a group IX atom or a group X atom, and specific examples thereof are a platinum atom or an iridium atom. Note that n=2 when M is the group IX atom, while n=1 when M is the group X atom.

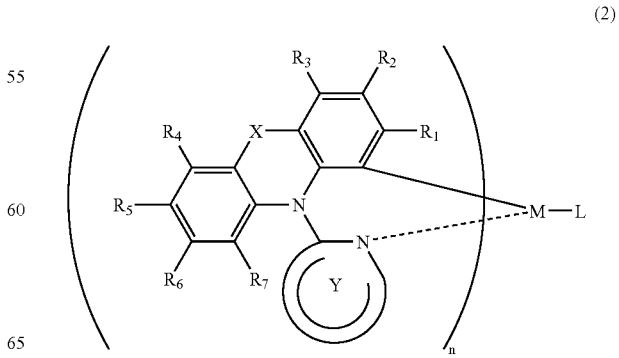

(2)

Any known synthesis method may be used as the cyclometallation reaction in this case. For instance, in the case of synthesizing the organometal complex of this invention having iridium as a central metal, a chlorine-bridged multinuclear complex is synthesized by mixing a hydrate of iridium chloride used as a central metal staple with the ligand of the general formula (12), and then by a heating reflux under a nitrogen atmosphere (the following synthesis scheme (b)). Then, by mixing the obtained multinuclear complex with the bidentate chelate ligand L and then refluxing the mixture under a nitrogen atmosphere, the chlorine bridge is cut by the bidentate chelate ligand L, thereby giving the organometal complex of this invention (the following synthesis scheme (c)).

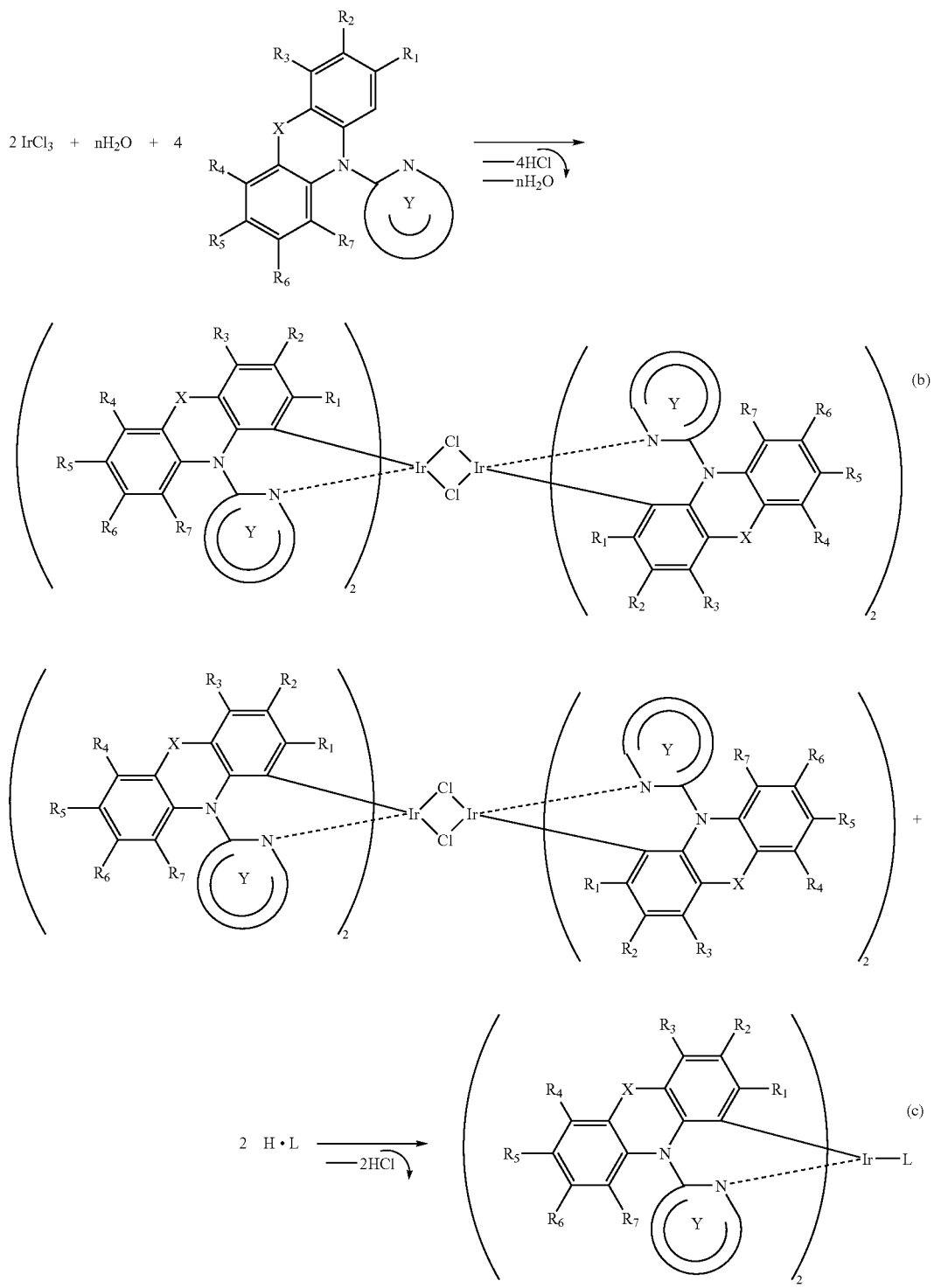

L represents any one of a monoanionic bidentate chelate ligand having a beta-diketone structure, a monoanionic bidentate chelate ligand having a carboxyl group, or a monoanionic bidentate chelate ligand having a phenolic hydroxyl group, and specific examples thereof are acetylacetone, dimethyl malonate, picolinic acid, proline, salicylidenamine, salicylaldehyde, 8-quinolinol, and the like.

Specific examples of the organometal complex of this invention in this way are those represented by the structural formulas (13) to (20) and the like. But the organometal complexes of this invention are not limited to them. In addition, though the trans-types are disclosed as the structural formulas (16) and (20), they may be the cis-type.

(13)
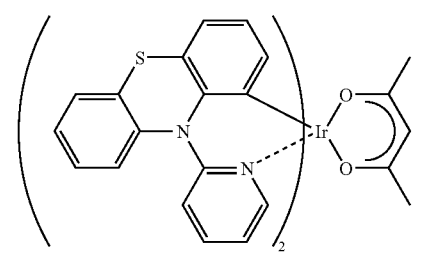

(14)
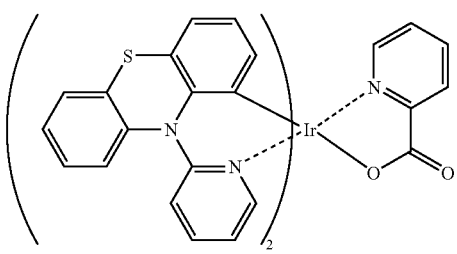

(15)
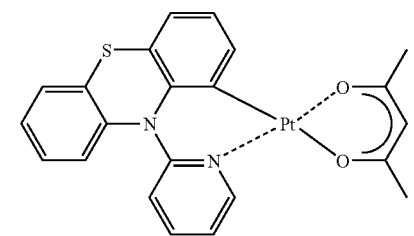

(16)
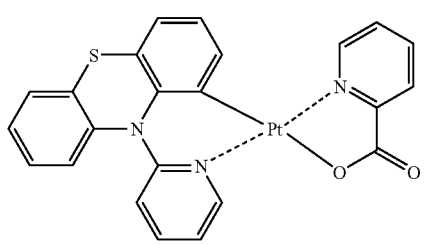

(17)
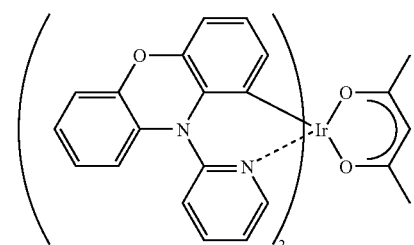

-continued

(18)
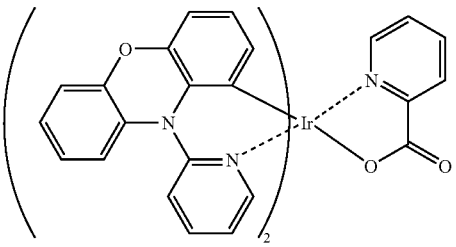

(19)
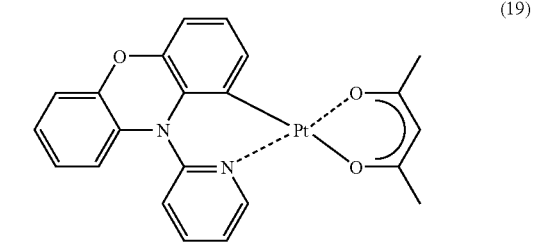

(20)
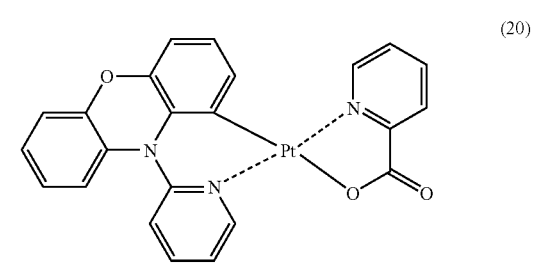

Though the structures using the bidentate chelate ligand L have been described by way of example in the foregoing, the organometal complexes of this invention are not limited thereto.

For instance, as represented by the following structural formulas (21) to (24), a ligand capable of orthometallation (2-phenylpyridine in the structural formulas (21) to (24)) may be used in place of the above-described bidentate chelate ligands L. It is possible to synthesize these organometal complexes by way of a product of the above-described reaction formula (c). For instance, it is possible to synthesize the organometal complex of the structural formula (21) by reacting the above-described structural formula (13) with 2-phenylpyridine. In addition, though the cis-types are disclosed as the structural formulas (22) and (24) in view of the fact that the cis-type is often formed in the cyclometal complex of platinum, they may be the trans-type.

(21)
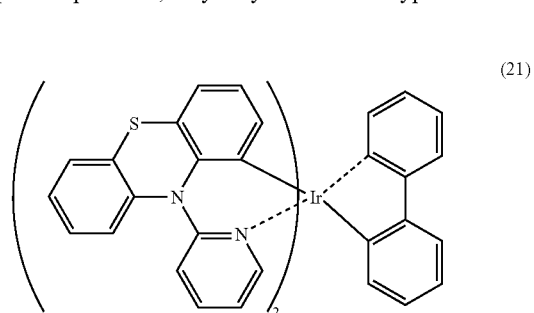

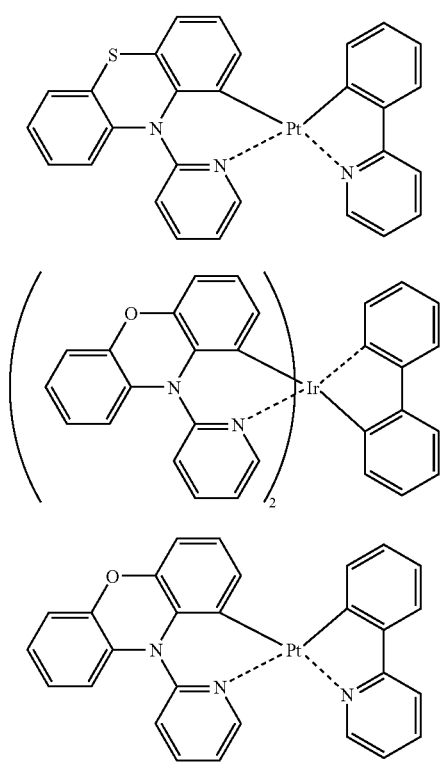

(22)

(23)

(24)

Alternatively, an identical ligand may be used as represented by the following structural formulas (25) to (28). It is also possible to synthesize these organometal complexes by way of the product of the above-described reaction formula (c). For instance, it is possible to obtain the organometal complex of the structural formula (25) by reacting the above-described structural formula (13) with 10-(2-pyridyl) phenothiazine. In addition, though the cis-types are disclosed as the structural formulas (26) and (28) in view of the fact that the cis-type is often formed in the cyclometal complex of platinum, they may be the trans-type.

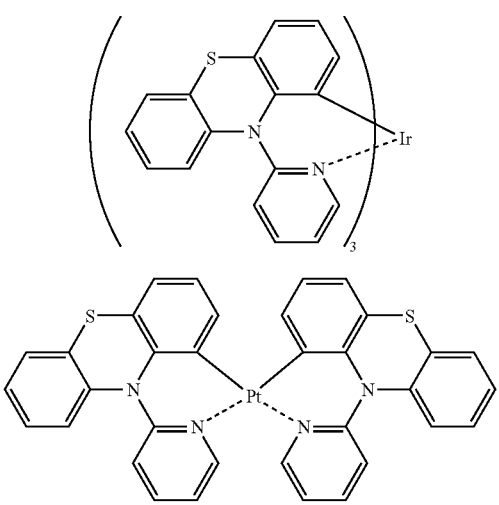

(25)

(26)

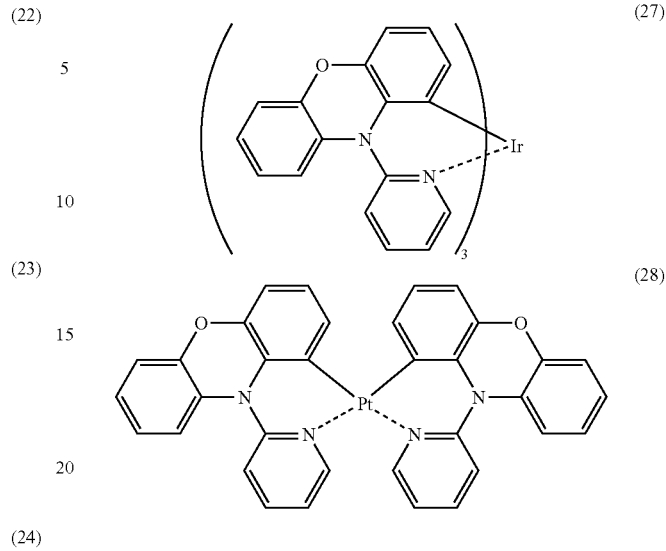

(27)

(28)

Though the above-described organometal complexes of this invention are usable as photosensitizers and phosphorescent materials, modes of applying them to electroluminescence elements will be described below.

The electroluminescence elements in this invention basically has an element structure that an electroluminescence layer (including at least a luminescent layer and a layer or a plurality of layers selected from a hole injection layer, a hole transport layer, a luminescent layer, a hole blocking layer, an electron transport layer, and an electron injection layer) containing the above-described organometal complex of this invention is sandwiched between a pair of electrodes (an anode and a cathode).

Also, apart from the organometal complexes of this invention, known materials may be used for the electroluminescence layer, and the known materials may be a low-molecular material or a high-molecular material. In addition, as the materials for forming the electroluminescence layer, those having a structure partially included an inorganic compound may be used in addition to those formed only from organic compound materials.

Hereinafter, embodiment modes of the electroluminescence elements of this invention will be described in detail.

EMBODIMENT MODE 1

In this Embodiment Mode 1, an element structure of an electroluminescence element having a luminescent layer containing the organometal complex of this invention, a hole injection layer formed from a low-molecular material, a hole transport layer, a hole blocking layer, and an electron transport layer will be described with reference to FIG. 1.

Referring to FIG. 1, the structure is such that a first electrode 101 is formed on a substrate 100, and an electroluminescence layer 102 and a second electrode 103 are formed on the first electrode 101 in this order.

A material to be used for the substrate 100 is not limited so far as it has been used for conventional electroluminescence elements, and examples thereof are glass, quartz, a transparent plastic, and the like.

In this Embodiment Mode 1, the first electrode 101 functions as an anode, and the second electrode 103 functions as a cathode.

That is, the first electrode 101 is formed from an anode material, and the anode material to be used may be preferably a metal, an alloy, an electroconductive compound, a mixture thereof, and the like having a large work function (work function 4.0 eV or more). Specific examples of the anode material are ITO (Indium Tin Oxide), IZO (Indium Zinc Oxide) obtained by mixing 2 to 20% of zinc oxide (ZnO) with indium oxide, gold (Au), platinum (Pt), nickel (Ni), tungsten (W), chrome (Cr), molybdenum (Mo), iron (Fe), cobalt (Co), copper (Cu), and palladium (Pd), or a nitride of a metal material (TiN), and the like.

In turn, a cathode material to be used for forming the second electrode 103 may be preferably a metal, an alloy, an electroconductive compound, a mixture thereof, and the like having a small work function (work function 3.8 eV or less). Specific examples of the cathode material are an element belonging to the first or second group of the periodic table of the elements, i.e. an alkali metal such as Li and Cs and an alkali earth metal such as Mg, Ca, and Sr; an alloy (Mg:Ag, Al:Li) and a compound (LiF, CsF, $CaF_2$) containing the alkali metal and the alkali earth metal; and a transition metal containing a rare earth metal, while it is possible to form the cathode by stacking metals (including alloys) such as Al, Ag, and ITO.

The above-described anode and cathode materials are formed into a thin film by vapor deposition, sputtering, or the like to form the first electrode 101 and the second electrode 103. A thickness of the film may be preferably from 10 to 500 nm.

Light generated by the recombination of carriers in the electroluminescence layer of the electroluminescence element of this invention emerges from one or both of the first electrode 101 and the second electrode 103 to outside. More specifically, the first electrode 101 is formed from a translucent material in the case where the light emerges from the first electrode 101, and the second electrode 103 is formed from a translucent material in the case where the light emerges from the second electrode 103.

The electroluminescence layer 102 is formed by stacking a plurality of layers, and, in this Embodiment Mode 1, a hole injection layer 111, a hole transport layer 112, a luminescent layer 113, a hole blocking layer 114, and an electron transport layer 115 are stacked to form the electroluminescence layer 102.

As a hole injection material to be used for forming the hole injection layer 111, a phthalocyanine-based compound is effective. For example, phthalocyanine (abbreviation: $H_2Pc$), copper phthalocyanine (abbreviation: CuPc), and the like may be used.

As a hole transport material to be used for forming the hole transport layer 112, an aromatic amine-based compound (more specifically, having a benzene ring-nitrogen bonding) may preferably be used. Examples of the material which is generally in use are 4,4'-bis[N-(3-methylphenyl)-N-phenyl-amino]-biphenyl (abbreviation: TPD), a derivative thereof such as 4,4'-bis[N-(1-naphthyl)-N-phenyl-amino]-biphenyl (abbreviation: α-NPD), a starburst aromatic amine compound such as 4,4',4''-tris(N,N-diphenyl-amino)-triphenylamine (abbreviation: TDATA), and 4,4',4''-tris[N-(3-methylphenyl)-N-phenyl-amino]-triphenylamine (abbreviation: MTDATA).

The luminescent layer 113 contains the organometal complex of this invention and is formed by deposition together with a host material. Known materials may be used as the host material, and examples thereof are 4,4'-bis(N-carbazolyl)-biphenyl (abbreviation: CBP), 2,2',2''-(1,3,5-benzentri-yl)-tris[1-phenyl-1 H-benzimidazole] (abbreviation: TPBI), and the like. Alternatively, the luminescent layer 113 may be formed of a layer consisting of the organometal complex of this invention.

As a hole blocking material to be used for forming the hole blocking layer 114, bis(2-methyl-8-quinolinolato)-4-phenylphenolato-aluminum (abbreviation: BAlq), 1,3-bis[5-(p-tert-butylphenyl)-1,3,4-oxadiazole-2-yl]benzene (abbreviation: OXD-7), 3-(4-tert-butylphenyl)$_4$-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and the like may be used.

As an electron transport material to be used for forming the electron transport layer 115, a metal complex having a quinoline skeleton or a benzoquinoline skeleton, such as tris(8-quinolinolato)aluminum (abbreviation: $Alq_3$), tris(5-methyl-8-quinolinolato)aluminum (abbreviation: $Almq_3$), bis(10-hydroxybenzo[h]-quinolinato)beryllium (abbreviation: $BeBq_2$), and BAlq listed above may be preferably used. Also, a metal complex having an oxazole-based or thiazole-based ligand, such as bis[2-(2-hydroxyphenyl)-benzooxazolato]zinc (abbreviation: $Zn(BOX)_2$), bis[2-(2-hydroxyphenyl)-benzothiazolato]zinc (abbreviation: $Zn(BTZ)_2$) may be used. Further, in addition to the metal complexes, 2-(4-biphenylyl)-5-(4-tert-butylphenyl)-1,3,4-oxadiazole (abbreviation: PBD) or OXD-7, TAZ, p-EtTAZ, BPhen, and BCP which are described above, and the like may be used as the electron transport material.

By using the above-described materials, it is possible to form the electroluminescence element having the luminescent layer 113 containing the organometal complex of this invention, the hole injection layer 111 formed from the low-molecular material, the hole transport layer 112, the hole blocking layer 114, and the electron transport layer 115.

In this Embodiment Mode 1, a color of the light emitted from the electroluminescence element is a color of light emission obtained from the organometal complex of this invention.

EMBODIMENT MODE 2

Figure 2:
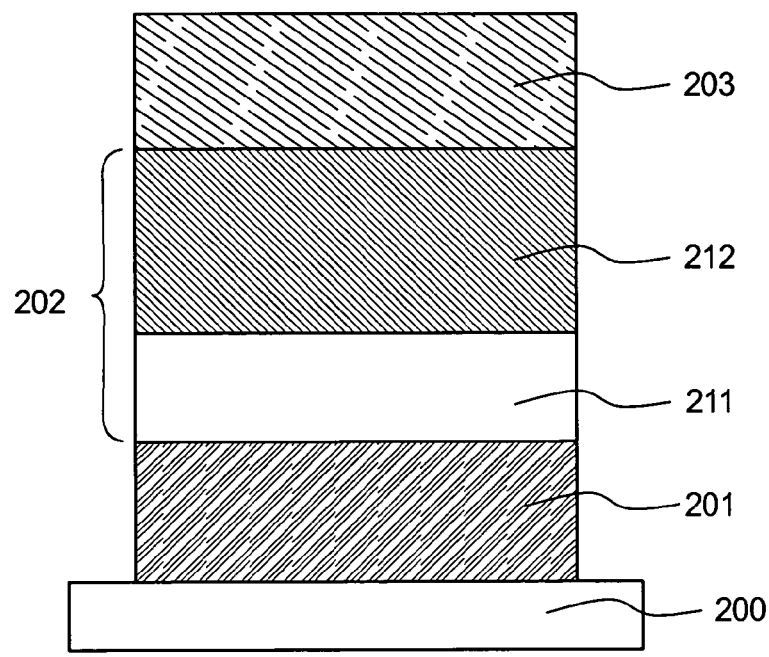
FIG. 2 is an illustration of an element structure of an electroluminescence element according to Embodiment Mode 2.

In this Embodiment Mode 2, an element structure of an electroluminescence element having a luminescent layer containing the organometal complex of this invention and a hole injection layer formed from a high-molecular material both of which layers are formed by wet processing will be described with reference to FIG. 2.

Since a substrate 200, a first electrode 201, and a second electrode 203 are formed by using the materials described in Embodiment Mode 1 and in the same manner as in Embodiment Mode 1, and then descriptions thereof are omitted.

An electroluminescence layer 202 is formed by stacking a hole injection layer 211 and a luminescent layer 212 in this Embodiment Mode 2.

As a hole injection material to be used for forming the hole injection layer 211, polyethylenedioxythiophene (abbreviation: PEDOT) which is doped with polystyrene sulfonic acid (abbreviation: PSS), polyaniline (abbreviation: PAni) doped with an accepter such as tetracyanoquinodimethane (abbreviation: TCNQ), polyvinylcarbazole (abbreviation: PVK), and the like may be used.

The luminescent layer 212 contains the organometal complex of this invention as a guest material. A host material is not limited so far as it is a bipolar material, and the bipolarity may be achieved by mixing the hole transport material and the electron transport material. For instance, it is possible to obtain the luminescent layer 212 by: dissolving a high-molecular compound (e.g. PVK) having a hole transport property and the above-described electron transport material (e.g. PBD) into same solvent at a molar ratio of 7:3; preparing a solution by adding a proper amount (about 5 wt %) of the organometal complex of this invention; and applying the solution by wet processing.

As described above, it is possible to obtain the electroluminescence element having the luminescent layer 212 containing the organometal complex of this invention and the hole injection layer 211 formed from the high-molecular material both of which layers are formed by the wet processing.

In this Embodiment Mode 2, a color of the light emitted from the electroluminescence element is a color of light emission obtained from the organometal complex of this invention.

EMBODIMENT MODE 3

Figure 3:
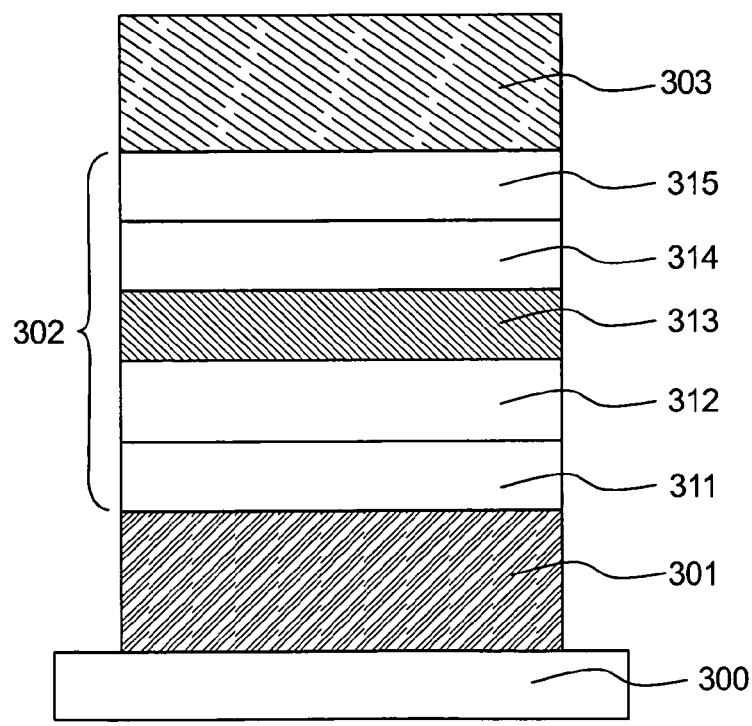
FIG. 3 is an illustration of an element structure of an electroluminescence element according to Embodiment Mode 3.

In this Embodiment Mode 3, an element structure of an electroluminescence element having a luminescent layer containing two types of guest materials which are the organometal complex of this invention and a fluorescent compound, a hole injection layer formed from a low-molecular material, a hole transport layer, a hole blocking layer, and an electron transport layer will be described with reference to FIG. 3.

Since it is possible to form a substrate 300, a first electrode 301, a second electrode 303, a hole injection layer 311, a hole transport layer 312, a hole blocking layer 314, and an electron transport layer 315 by using the materials described in Embodiment Mode 1 and in the same manner as described in Embodiment Mode 1, and then descriptions thereof are omitted.

In this Embodiment Mode 3, an electroluminescence layer 302 is formed by stacking the hole injection layer 311, the hole transport layer 312, a luminescent layer 313, the hole blocking layer 314, and the electron transport layer 315.

The luminescent layer 313 of this Embodiment Mode is formed from a host material, the organometal complex of this invention which is a first guest material, and the fluorescent compound which is a second guest material. As the host material, the materials described in Embodiment Mode 1 may be used.

As the second guest material, known fluorescent compound may be used, and specific examples thereof are DCM1, DCM2, DCJTB, quinacridone, N,N-dimethylquinacridone, rubrene, perylene, DPT, Co-6, PMDFB, BTX, ABTX, and the like.

In this Embodiment Mode 3, and as is the case with the Non-Patent Document 6, the organometal complex of this invention which is the first guest material functions as a substance causing a sensitizing action in the luminescent layer 313 so as to amplify the volume of a singlet excitation state of the fluorescent compound which is the second guest material. Therefore, the electroluminescence element of this Embodiment Mode 3 is the light emission element wherein a color of emitted light is a color of light emission obtained from the fluorescent compound, and a light emission efficiency thereof can be improved as compared with a conventional electroluminescence element using the fluorescent compound.

EMBODIMENTS

Hereinafter, the embodiment modes of this invention will be described with reference to the drawings. Note that it is possible to practice this invention in various different modes, and person skilled in the art will easily understand that the embodiment modes and details of this invention can be modified without departing from spirit and scope of this invention. Therefore, this invention should not be limited to the contents described in the embodiment modes.

SYNTHESIS EXAMPLE 1

In this synthesis example, a synthesis of the organometal complex (abbreviation: $Ir(ppt)_2(acac)$) of this invention represented by the above-described structural formula (13) will be described.

[Step 1: Synthesis of Ligand (ppt)]

To start with, 2.35 g (11.8 mmol) of phenothiazine (product of Tokyo Kasei Kogyo Co., Ltd.), 3.63 g (17.7 mmol) of 2-iodopyridine (product of Tokyo Kasei Kogyo Co., Ltd.), 6.5 g of potassium carbonate, 1.5 g of copper powder, and 0.31 g of 18-crown-6-ether were mixed with the use of 20 ml of o-dichlorobenzene as a solvent, followed by reflux under a nitrogen atmosphere for 16 hours. After that, copper and inorganic salt were removed and then column purification using a toluene solvent was performed to give a ligand ppt (10-(2-pyridyl)phenothiazine) (opaque white powder; yield: 70%). A summary of the synthesis scheme is shown in the following (a-1).

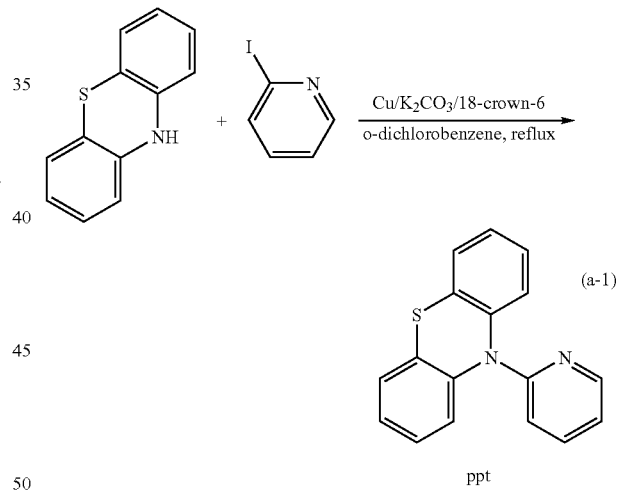

From a measurement of an IR absorption spectrum of the obtained opaque white powder, it was found that N—H stretching vibration (3340 cm$^{-1}$) caused by phenothiazine was lost, and the finding suggests a progress of the reaction.

[Step 2: Synthesis of Multinuclear Complex ($[Ir(Ppt)_2Cl]_2$)]

Next, 1.19 g (4.3 mmol) of ppt obtained as described above and 0.50 g (1.7 mmol) of iridium chloride ($IrCl_3 \cdot HCl \cdot H_2O$) (product of Kishida Chemical Co., Ltd.) were mixed with the use of a mixed solution of 30 ml of 2-ethoxyethanol and 10 ml of water as a solvent, followed by reflux under a nitrogen atmosphere for 18 hours, thereby giving a multinuclear complex ($[Ir(ppt)_2Cl]_2$ (yellow powder; yield: 70%). A summary of the synthesis scheme is shown in the following (b-1).

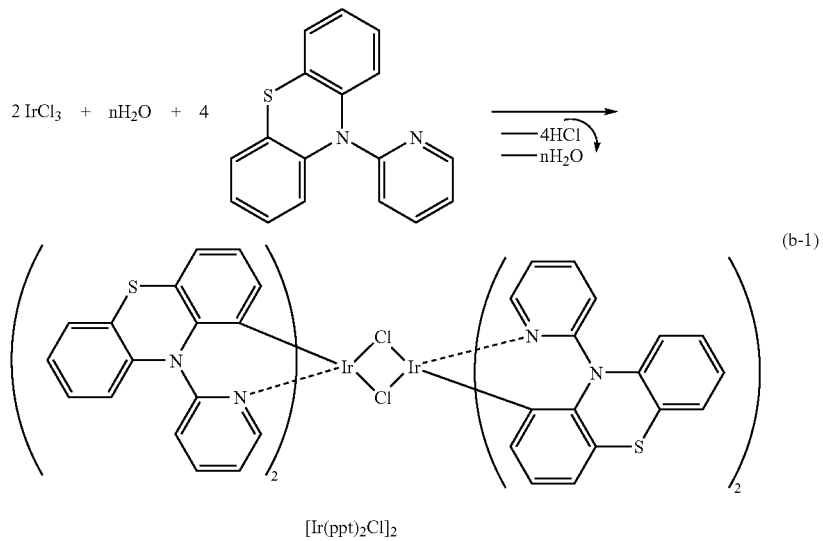

[Ir(ppt)$_2$Cl]$_2$

[Step 3: Synthesis of the Organometal Complex (Ir(ppt)$_2$(acac)) of this Invention]

Further, 0.78 g (0.50 mmol) of [Ir(ppt)$_2$Cl]$_2$ obtained as described above, 0.15 ml (1.5 mmol) of acetylacetone, and 0.53 g of sodium carbonate were mixed with the use of 30 ml of 2-ethoxyethanol as a solvent, followed by reflux under a nitrogen atmosphere for 18 hours. The obtained yellow powder was subjected to a column purification using dichloromethane as a solvent to give the organometal complex Ir(ppt)$_2$(acac) of this invention (yellow powder; yield: 60%). A summary of the synthesis scheme is shown in the following (c-1).

molecular weight: 842). Further, similar isotope ions are observed at m/z863, 864, 865, 866, and 867 as Na adducts of Ir(ppt)$_2$(acac). A pattern of ionic strength of these isotope peaks was similar to a result of logical calculation. Therefore, it was considered that the organometal complex Ir(ppt)$_2$(acac) of this invention as shown in the above-described structural formula (13) was obtained.

Further, a measurement result of 1H-NMR(DMSO-d6) was as follows.

δ/ppm=8.29 (d, 2H), 7.69 (t, 2H), 7.46 (t, 2H), 7.16 (d, 2H), 7.08 (t, 2H) 2H), 6.90 (t, 2H), 6.71 (d, 4H), 6.62 (d, 2H), 6.46 (d, 2H), 5.74 (s, 1H), 1.93 (s, 6H).

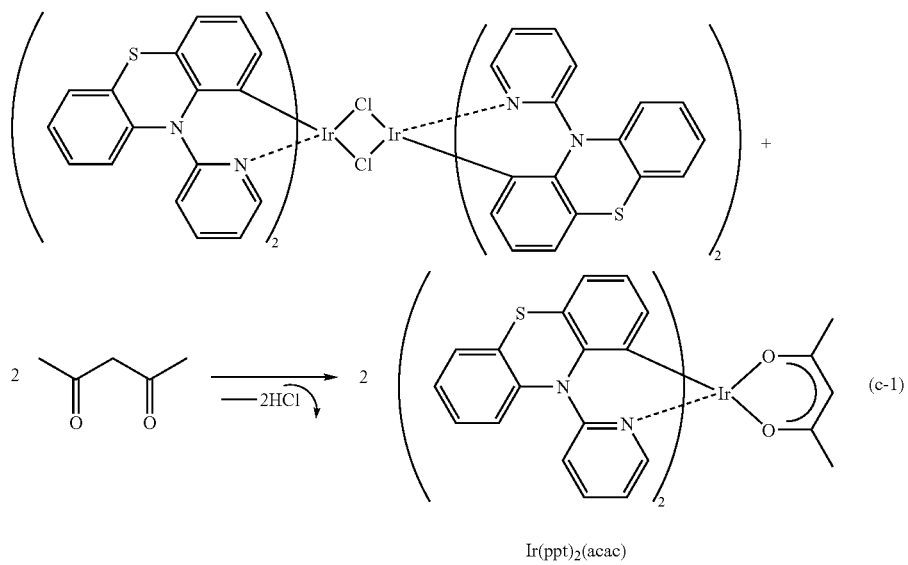

Ir(ppt)$_2$(acac)

From a mass analysis (ESI-MS) of the obtained yellow powder, isotope ions were observed at m/z840, 841, 842, 843, and 844 which are close to a molecular weight of Ir(ppt)$_2$(acac) (composition formula: $C_{39}H_{29}IrN_4O_2S_2$;

Also, from a measurement of a decomposition temperature $T_d$ by TG-DTA in the organometal complex Ir(ppt)$_2$(acac) of this invention, $T_d$=337° C. was found to reveal that the organometal complex exhibits good heat resistance.

Further, the yield was good as described above to reveal that the organometal complex is also good from the cost point of view.

Figure 6:
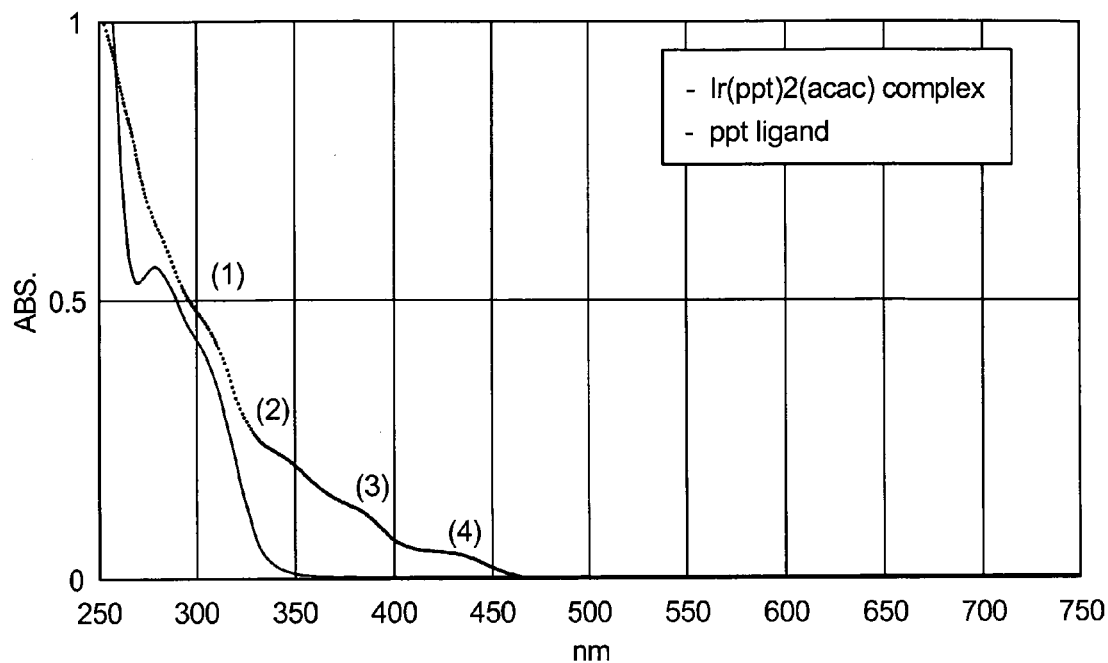
FIG. 6 is a diagram showing a UV-Vis absorption spectrum of the organometal complexes of this invention.

Next, an absorption spectrum of Ir(ppt)$_2$(acac) in dichloroethane is shown in FIG. 6. Note that an absorption spectrum of the ligand ppt is also shown in FIG. 6. The ligand ppt has its absorption peak near 280 nm and 300 nm. In turn, the organometal complex Ir(ppt)$_2$(acac) of this invention has its absorption peak at 4 points, i.e. near (1) 300 nm, (2) 350 nm, (3) 380 nm, and (4) 425 mm.

The absorption peak (1) is a singlet π-π* transition due to the ligand because it is almost the same as the absorption of the ligand ppt. The absorption peaks of (2), (3), and (4) are those often found with the orthometal complexes and specific to the organometal complexes, which are analogized to be equivalent to a singlet MLCT transition, a triplet π-π* transition, a triplet MLCT transition, and the like. Particularly, the absorption peak (4) is considered to be the absorption spectrum specific to the triplet MLCT transition since it has a broad bottom in the visible region. That is to say, it was found that Ir(ppt)$_2$(acac) is a compound capable of direct photoexcitation to the triplet excitation state and intersystem crossing.

Figure 7:
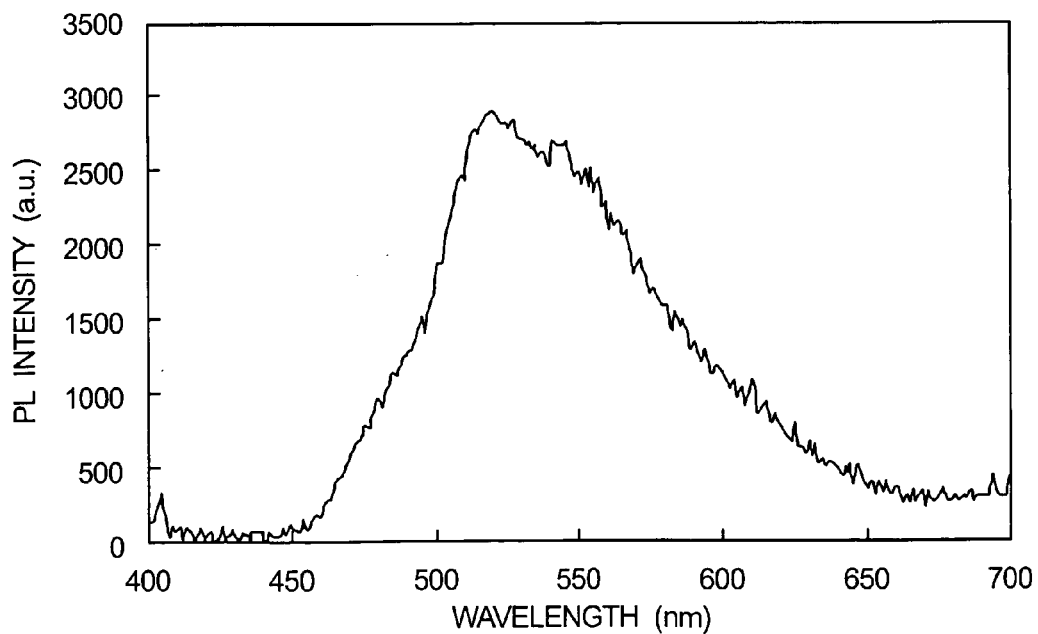
FIG. 7 is a diagram showing a light emission spectrum of the organometal complex of this invention.

Shown in FIG. 7 is a light emission spectrum (photoluminescence) of the Ir(ppt)$_2$(acac) powder. Excitation light was set to 365 nm. As shown in FIG. 7, green light emission having a light emission peak at 520 nm at a room temperature was exhibited. In view of the absorption spectrum of FIG. 6, this is considered to be phosphorescence.

COMPARATIVE EXAMPLE 1

A conventional iridium complex (abbreviation: Ir(tpy)$_2$(acac)) represented by the following structural formula (29) was synthesized, and a decomposition temperature $T_d$ thereof measured by TG-TDA was 298° C.

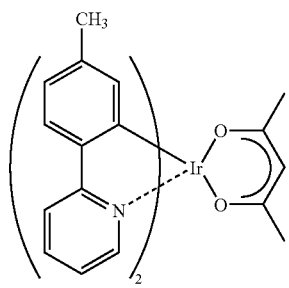

(29)

The organometal complex Ir(ppt)$_2$(acac) of this invention described in Synthesis Example 1 has $T_d$ of 337° C., and the results reveal that $T_d$ of the conventional iridium complex Ir(tpy)$_2$(acac) is lower than that of Ir(ppt)$_2$(acac) by nearly 40° C. Thus, it was revealed that the organometal complex of this invention is also excellent in heat resistance.

SYNTHESIS EXAMPLE 2

In this synthesis example, a synthesis of the organometal complex (abbreviation: Ir(ppx)$_2$(acac)) of this invention represented by the structural formula (17) will be described by way of example.

[Step 1: Synthesis of Ligand (ppx)]

To start with, 1.73 g of phenoxazine, 2.90 g of 2-iodopyridine, 5.24 g of potassium carbonate, 1.2 g of copper powder, and 0.25 g of 18-crown-6-ether were mixed with the use of 20 ml of ortho-dichlorobenzene as a solvent, followed by reflux under a nitrogen atmosphere for 8 hours. After that, copper and inorganic salt were removed, and then column purification using a dichloromethane solvent was performed to give a ligand ppx (1-(2-pyridyl)phenoxazine) (white powder; yield: 91%). A summary of the synthesis scheme is shown in the following (a-2).

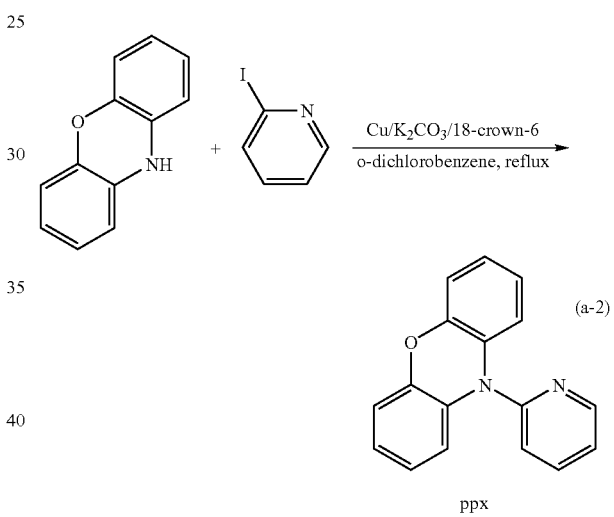

(a-2)

ppx

[Step 2: Synthesis of Multinuclear Complex ([Ir(ppx)$_2$Cl]$_2$)]

Next, 2.18 g of ppx obtained as described above and 1.00 g of iridium chloride (IrCl$_3$.HCl.H$_2$O) were mixed with the use of a mixed solution of 30 ml of 2-ethoxyethanol and 10 ml of water as a solvent, followed by reflux under a nitrogen atmosphere for 14 hours, thereby giving a multinuclear complex [Ir(ppx)$_2$Cl]$_2$ (yellow powder; yield: 96%). A summary of the synthesis scheme is shown in the following (b-2).

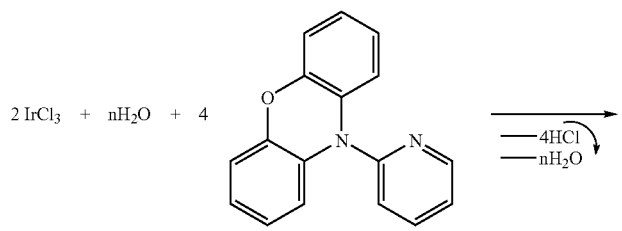

-continued

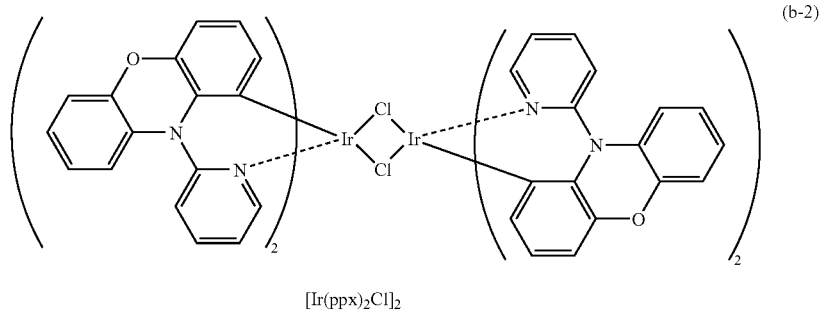

(b-2)

[Ir(ppx)$_2$Cl]$_2$

[Step 3: Synthesis of the Organometal Complex (Ir(ppx)$_2$(acac) of this Invention)]

Further, 1.00 g of [Ir(ppx)$_2$Cl]$_2$ obtained as described above, 0.21 ml of acetylacetone (Hacac), and 0.71 g of sodium carbonate were mixed with the use of 30 ml of 2-ethoxyethanol as a solvent, followed by reflux under a nitrogen atmosphere for 14 hours. The obtained solid was washed with water, ethanol, and an ether solution to give the organometal complex Ir(ppx)$_2$(acac) (yellow powder; yield: 87%). A summary of the synthesis scheme is shown in the following (c-2).

Figure 8:
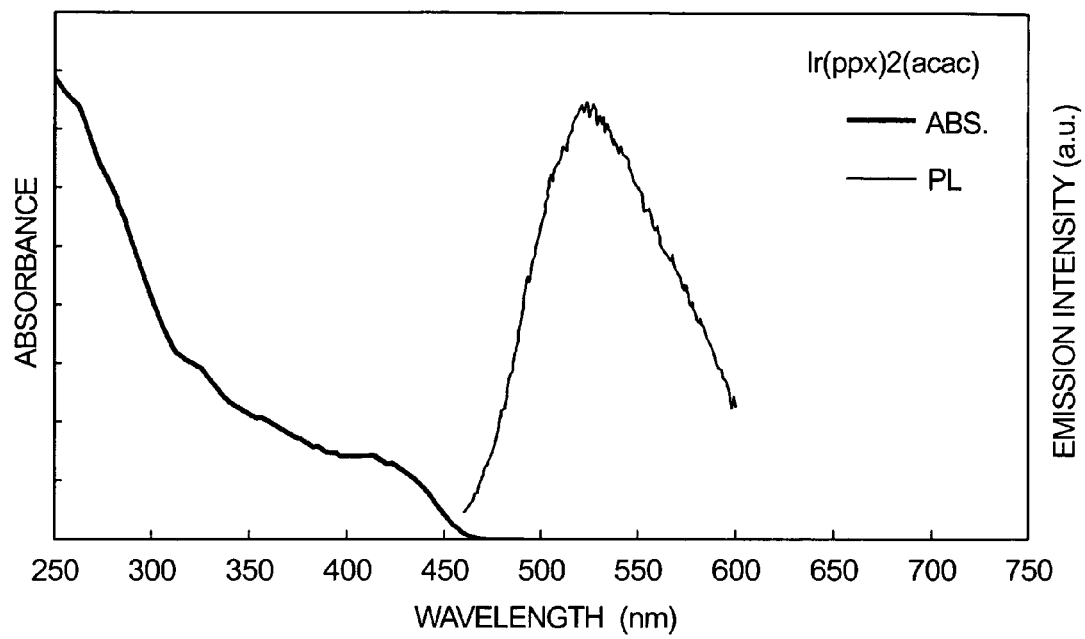
FIG. 8 is a diagram showing a UV-Vis absorption spectrum and a light emission spectrum of the organometal complexes of this invention.

Next, an absorption spectrum and a light emission spectrum (photoluminescence) of Ir(ppx)$_2$(acac) in dichloromethane are shown in FIG. 8. The organometal complex Ir(ppx)$_2$(acac) of this invention has its absorption peak at 256 nm, 314 nm, 348 nm, and 410 nm, and, as was the case with Synthesis Example 1, the absorption peaks are those often found with the orthometal complexes and specific to the organometal complexes. A peak of the light emission spectrum was at 524 nm, and a color of the light emission was green.

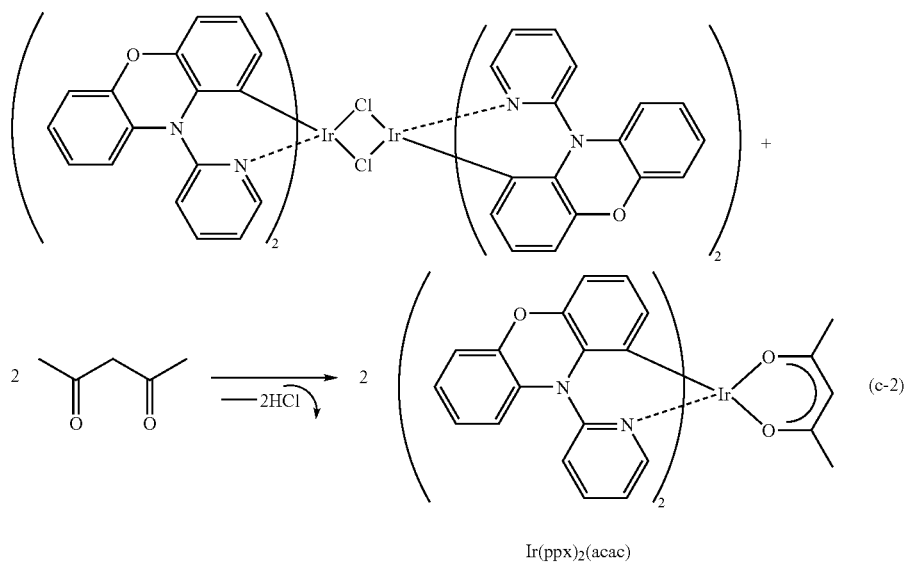

Ir(ppx)$_2$(acac)

Also, from a measurement of a decomposition temperature $T_d$ by TG-DTA in the obtained organometal complex Ir(ppx)$_2$(acac) of this invention, $T_d=345°$ C. was detected to reveal that the organometal complex exhibits good heat resistance as compared with Ir(tpy)$_2$(acac) of Comparative Example 1 ($T_d=298°$ C.). Further, the yield was good as described above to reveal that the organometal complex is also excellent from the cost point of view.

Further, a measurement result of 1H-NMR(DMSO-d$_6$) was as follows.

δ/ppm=7.78 (d, 2H), 7.69 (t, 2H), 7.31 (d, 2H), 7.20 (m, 6H), 7.01 (d, 2H), 6.79 (t, 2H), 6.50 (d, 2H), 6.39 (t, 2H), 5.61 (d, 2H), 4.97 (s, 1H), 1.62 (s, 6H).

SYNTHESIS EXAMPLE 3

In this synthesis example, a synthesis of the organometal complex (abbreviation: Ir(ppx)$_2$(pic)) of this invention represented by the above-described structural formula (18) will be described by way of example. As a staple, the multi-nuclear complex [Ir(ppx)$_2$Cl]$_2$ obtained in Step 2 of Synthesis Example 2 described above was used.

To start with, 1.00 g of [Ir(ppx)$_2$Cl]$_2$, 0.25 ml of picolinic acid (pic), and 0.71 g of sodium carbonate were mixed with the use of 30 ml of 2-ethoxyethanol as a solvent, followed by reflux under a nitrogen atmosphere for 14 hours. The obtained solid was washed with water, ethanol, and an ether solution to give the organometal complex Ir(ppx)$_2$(pic) of this invention (yellow powder; yield: 72%). A summary of the synthesis scheme is shown in the following (c-3).

A substrate 100 on which 110 nm in thickness of an indium tin oxide (ITO) is formed was used as the first electrode 101. The size of the first electrode 101 was 2-mm-square. 20 nm of a CuPc film was formed on the first

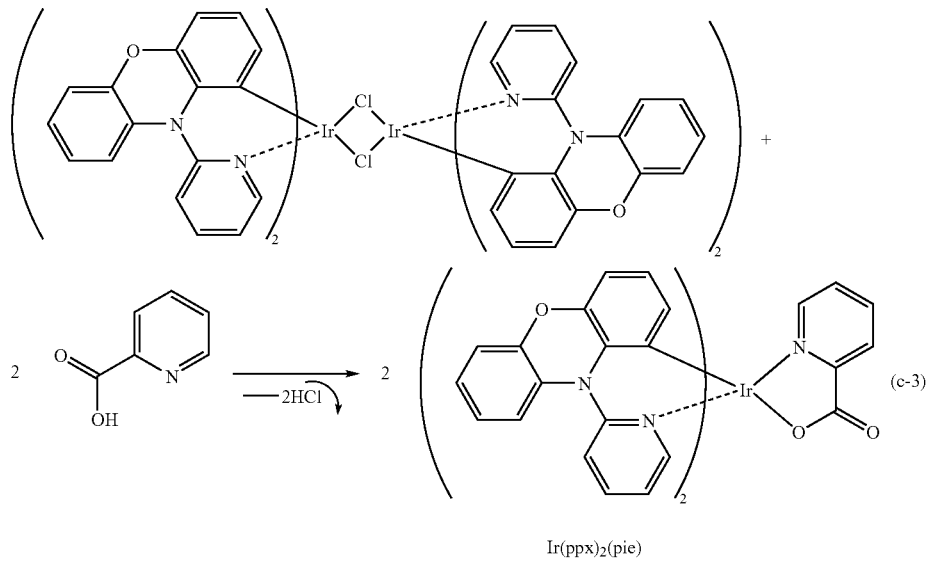

Ir(ppx)$_2$(pie)

30

From a measurement of a decomposition temperature $T_d$ by TG-DTA in the organometal complex Ir(ppx)$_2$(pic) of this invention, $T_d$=396° C. was detected to reveal that the organometal complex has good heat resistance as compared with Ir(tpy)$_2$(acac) of Comparative Example 1 ($T_d$=298° C.). Further, the yield was good as described above to reveal that the organometal complex is also excellent from the cost point of view.

Further, a measurement result of 1H-NMR(DMSO-d6) was as follows.

δ/ppm=8.57 (d, 1H), 8.00 (t, 1H), 7.89 (d, 2H), 7.75 (d, 1H), 7.63 (d, 2H), 7.33 (m, 2H), 7.24 (m, 5H), 7.11 (m, 2H), 7.00 (t, 1H), 6.81 (t, 1H), 6.64 (m, 4H), 6.45 (t, 1H), 6.22 (d, 1H), 5.86 (d, 1H), 5.49 (d, 1H).

Figure 9:
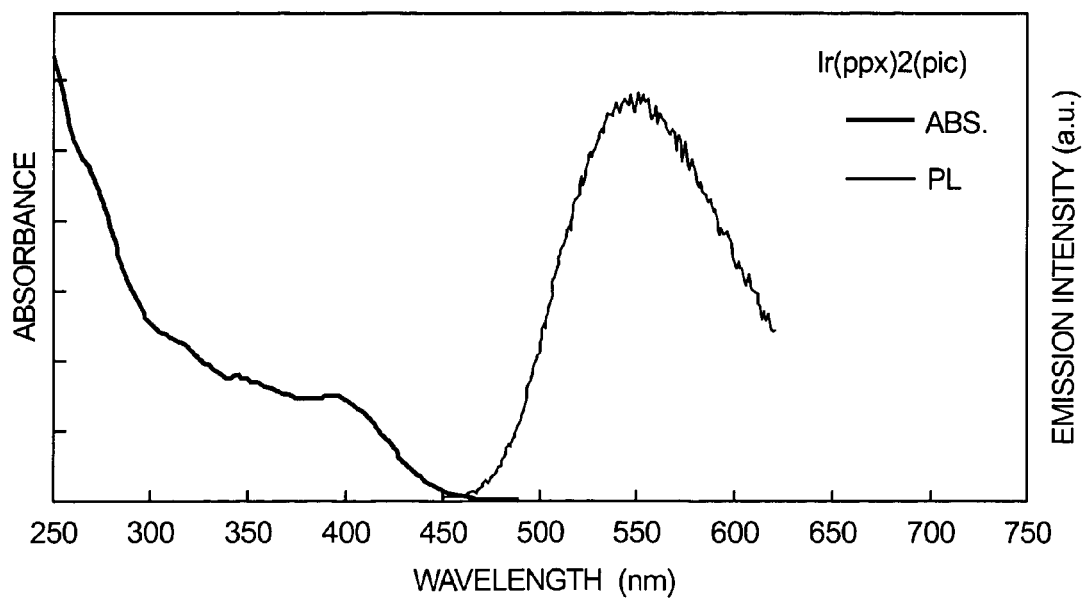
FIG. 9 is a diagram showing a UV-Vis absorption spectrum and a light emission spectrum of the organometal complexes of this invention.

Next, an absorption spectrum and a light emission spectrum (photoluminescence) in dichloromethane of Ir(ppx)$_2$(pic) are shown in FIG. 9. The organometal complex Ir(ppx)$_2$(pic) of this invention has its absorption peak at 226 nm, 314 nm, 338 nm, and 396 nm, and, as was the case with Synthesis Example 1, the absorption peaks are those often found with the orthometal complexes and specific to the organometal complexes. A peak of the light emission spectrum was at 551 nm, and a color of the light emission was yellow green.

EMBODIMENT 1

In this embodiment, an electroluminescence element using the organometal complex Ir(ppx)$_2$(acac) of this invention which is represented by the above-described structural formula (17) and obtained in Synthesis Example 2 as an illuminant will be described as a specific example. The structure shown in FIG. 1 was applied as an element structure, and vapor deposition was used as a film formation method. In this embodiment, a first electrode 101 serves as an anode and a second electrode 103 serves as a cathode.

electrode 101 as a hole injection layer 111, and then 30 nm of an α-NPD film was formed as a hole transport layer 112.

By depositing CBP and Ir(ppx)$_2$(acac) together, 30 nm of a luminescent layer 113 was formed on the hole transport layer 112. During the film formation, a deposition rate was adjusted so as to keep a content of Ir(ppx)$_2$(acac) in the luminescent layer 113 at about 8 wt %.

Next, 10 nm of a BCP film was formed as a hole blocking layer 114, and then 20 nm of an Alq$_3$ film was formed as an electron transport layer 115. The layers described above correspond to an electroluminescence layer 102. Lastly, the second electrode 103 was formed by forming 2 nm of a calcium fluoride film and 100 nm of an aluminum film.

Figure 10A:
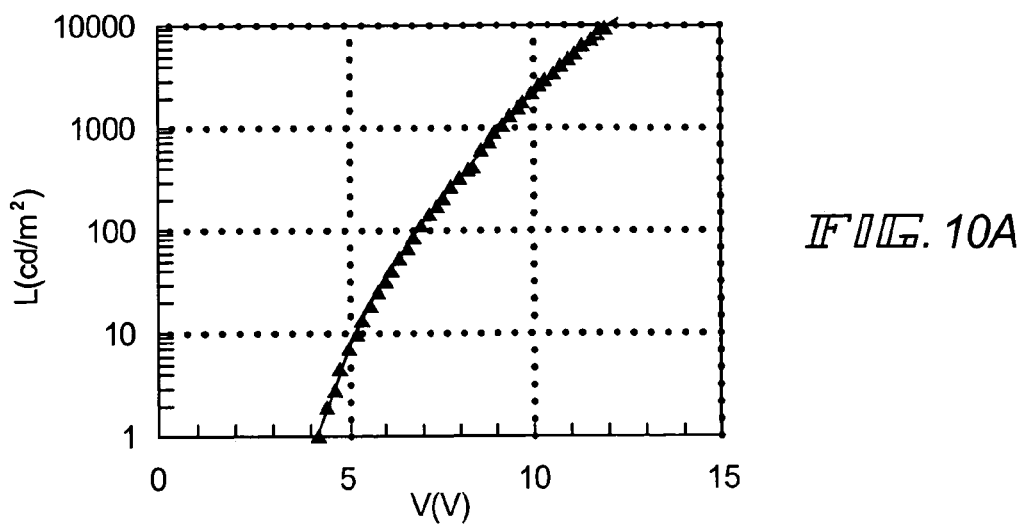
FIG. 10 is a diagram showing characteristics of the electroluminescence element of this invention.
Figure 10B:
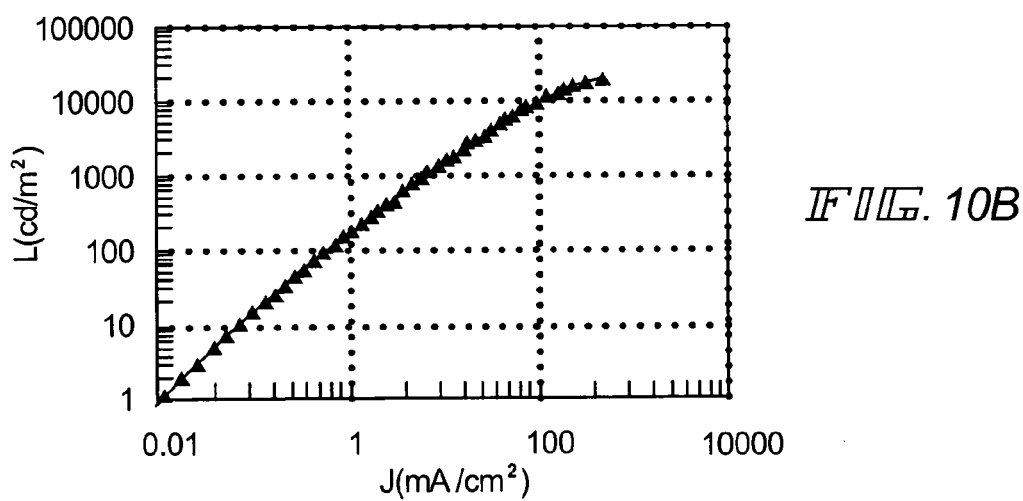
Figure 10C:
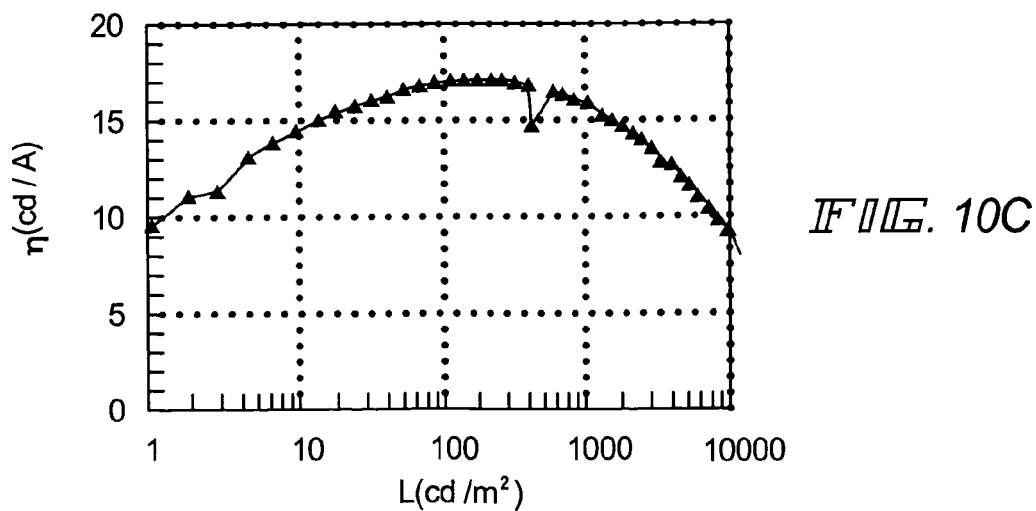

Element characteristics of this embodiment are shown in FIG. 10. Shown in FIG. 10(*a*) is a luminosity-voltage characteristic; shown in FIG. 10(*b*) is a luminosity-current density characteristic; and shown in FIG. 10(*c*) is a current efficiency-luminosity characteristic. This element emitted light having a luminosity of 118 cd/m$^2$ when a current having a current density of 0.694 mA/cm$^2$ was supplied thereto by a voltage application of 7.0 V. Also, current efficiency at the light emission was 17.0 cd/A, and external quantum efficiency was about 5.5%. Thus, high efficiency which was well above that of an electroluminescence element using light emission (fluorescence) from the singlet excitation state was obtained. This is considered to be attributable to the fact that the electroluminescence element of this invention exhibits the light emission (phosphorescence) from the triplet excitation state.

Figure 11:
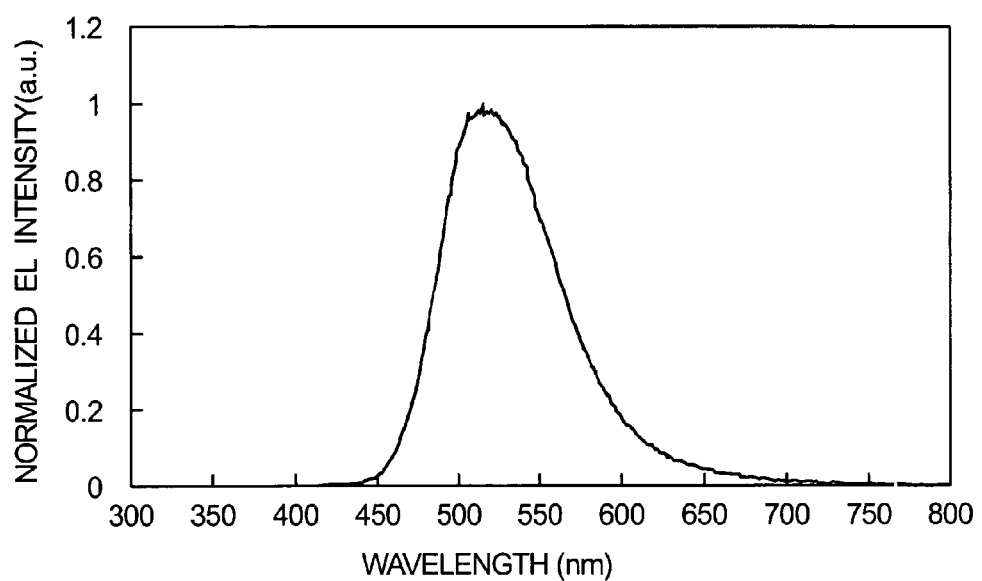
FIG. 11 is a diagram showing a light emission spectrum of the electroluminescence element of this invention.

Shown in FIG. 11 is a light emission spectrum of the electroluminescence element of this embodiment. As shown in FIG. 11, a green light emission having a peak at about 520 nm was detected. This is almost the same as the light emission spectrum of Ir(ppx)$_2$(acac) in solution shown in FIG. 8, and such similarity suggests that Ir(ppx)$_2$(acac)

emits the light in this embodiment. In addition, CIE chromaticity coordinates were (x, y)=(0.27, 0.60).

EMBODIMENT 2

In this embodiment, a light emission device having the electroluminescence element of this invention in a pixel portion will be described with reference to FIG. 4. FIG. 4(A) is a top view showing the light emission device, and FIG. 4(B) is a sectional view taken along the section A–A' of FIG. 4A. A source driving circuit is denoted by 401; a pixel portion is denoted by 402; and a gate driving circuit is denoted by 403, each of which is indicated by a dotted line. 404 denotes a sealing substrate; 405 denotes a sealant; and an inner side region enclosed by the sealant 405 is a space 407.

A leading wiring 408 serves to transmit signals input to the source driving circuit 401 and the gate driving circuit 403 and receives a video signal, a clock signal, a start signal, a reset signal, and the like from an FPC (Flexible Printed Circuit) 409 serving as an external input terminal. In addition, though only the FPC is indicated in the drawing, a printed wiring board (PWB) may be attached to the FPC. In this description, the light emission device includes the body of the light emission device as well as the light emission device on which the FPC or the PWB is mounted.

Next, a sectional structure will be described using FIG. 4(B). The driving circuit portion and the pixel portion are formed on a substrate 410, and the source driving circuit 401 included in the driving circuit portion and the pixel portion 402 are shown in the drawing.

As the source driving circuit 401, a CMOS circuit which is obtained by combining an n-channel type TFT 423 and a p-channel type TFT 424 is formed. The TFT forming the driving circuit may be a known CMOS circuit, PMOS circuit or NMOS circuit. Though the driver-integrated type, which the driving circuit is formed on the substrate, is used in this embodiment mode, the driving circuit may be formed outside the substrate.

The pixel portion 402 is formed of a plurality of pixels each having a switching TFT 411, a current control TFT 412, and a first electrode 413 electrically connected to a drain of the current control TFT 412. An insulator 414 is formed to cover an edge of the first electrode 413. The insulator 414 is formed by using a positive type photosensitive acryl resin film.

In order to achieve a good coverage, a curved surface having a curvature is formed on an upper end portion or a lower end portion of the insulator 414. For instance, in the case of using the positive type photosensitive acryl as a material for forming the insulator 414, it is preferable to form a curved surface having a curvature radius (0.2 μm to 3 μm) only on the upper end portion of the insulator 414. In addition, as the insulator 414, either one of a negative type which becomes insoluble to an etchant by a photosensitive light and a positive type which becomes soluble to an etchant by light may be used.

On the first electrode 413, an electroluminescence layer 416 and a second electrode 417 are formed. It is desirable to use a material having a large work function as a material for forming the first electrode 413 functioning as the anode. For instance, a single layer film such as an ITO (indium tin oxide) film, an indium zinc oxide (IZO) film, a titanium nitride film, a chromium film, a tungsten film, a Zn film, and a Pt film, a stack of a film mainly containing titanium nitride and a film mainly comprising aluminum, a three layer structure of a titanium nitride film, a film mainly containing aluminum, and a titanium nitride film, and the like may be used. The stack structure reduces a resistance of the wiring and achieves a good ohmic contact, so that the stack structure is capable of functioning as the anode.

The electroluminescence layer 416 is formed by a deposition method using a deposition mask or an ink jet method. A part of the electroluminescence layer 416 is formed by using the organometal complex of this invention, and a material to be used in combination may be either one of a low-molecular material and a high-molecular material. Further, though a single layer of an organic compound or a stack of organic compound layers is generally used as a material to be used for the electroluminescence layer, this invention encompasses a constitution which an inorganic compound is used for a part of a film formed from an organic compound.

As a material to be used for the second electrode (cathode) 417 formed on the electroluminescence layer 416, a material having a small work function (Al, Ag, Li, Ca, or an alloy thereof such as MgAg, MgIn, AlLi, $CaF_2$, or CaN) may be used. In the case where light generated in the electroluminescence layer 416 passes through the second electrode 417, a stack of a metal thin film having a low film thickness and a translucent conductive film (ITO (indium oxide tin oxide alloy), indium oxide zinc oxide alloy ($In_2O_3$—ZnO), zinc oxide (ZnO), etc.) may preferably be used as the second electrode (cathode) 417.

By joining the sealing substrate 404 and the element substrate 410 with the sealant 405, a constitution where the electroluminescence element 418 is provided in the space 407 enclosed by the substrate 410, the sealing substrate 404, and the sealant 405 is formed. Constitutions wherein the space 407 is filled with an inert gas (nitrogen or argon) and the space 407 is filled with the sealant 405 are encompassed by this invention.

It is preferable to use an epoxy-based resin as the sealant 405. Also, it is desirable that the material to be used should not permeate moisture and oxygen as far as possible. Further, as a material to be used for the sealing substrate 404, a glass substrate, a quartz substrate, and a plastic substrate made from FRP (Fiberglass-Reinforced Plastics), PVF (polyvinyl fluoride), mylar, polyester, or acryl may be used.

Thus, it is possible to obtain the light emission device having the electroluminescence element of this invention.

EMBODIMENTS 3

In this embodiment, various electric appliances completed by using the light emission device having the electroluminescence element of this invention will be described.

Examples of the electric appliances manufactured by using the light emission device having the electroluminescence element of this invention are a video camera, a digital camera, a goggle type display (head-mounted display), a navigation system, an audio reproduction apparatus (car audio, audio compo, etc.), a notebook type personal computer, a game machine, a personal digital assistant (mobile computer, mobile phone, mobile game machine, electronic book, etc.), an image reproduction apparatus having a recording medium (specifically, an apparatus capable of reproducing the recording medium such as a digital versatile disk (DVD) and having a display device capable of displaying images recorded on the DVD), and the like. Specific examples of these electric appliances are shown in FIG. 5.

Figure 5A:
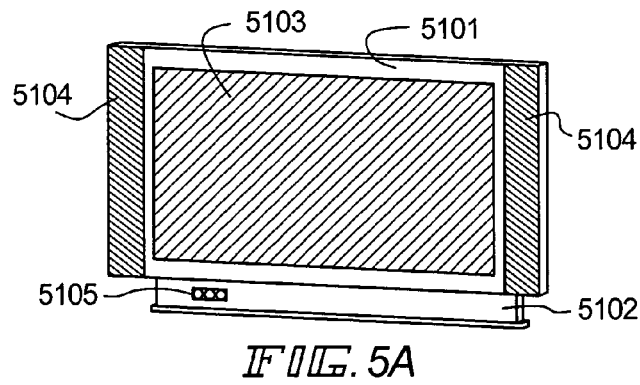
FIGS. 5A–5G are illustrations of electric appliances.

Shown in FIG. 5(A) is a display device which includes a housing 5101, a support 5102, a display portion 5103, speaker portions 5104, a video input terminal 5105, and the like. This is manufactured by using the light emission device having the electroluminescence element of this invention as the display portion 5103. In addition, the display device includes all information display devices such as a personal computer, a TV broadcast reception, an advertisement display.

Figure 5B:
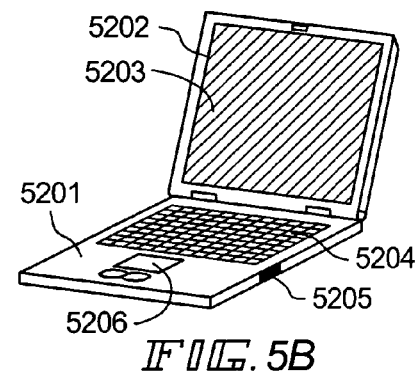

Shown in FIG. 5(B) is a notebook type personal computer which includes a body 5201, a housing 5202, a display portion 5203, a keyboard 5204, an external connection port 5205, a pointing mouse 5206, and the like. The display portion 5203 is manufactured by using the light emission device having the electroluminescence element of this invention.

Figure 5C:
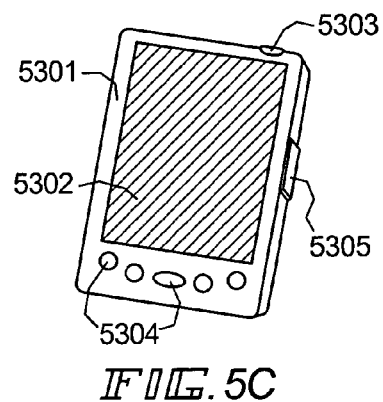

Shown in FIG. 5(C) is a mobile computer which includes a body 5301, a display portion 5302, a switch 5303, operation keys 5304, an infrared port 5305, and the like. The display portion 5302 is manufactured by using the light emission device having the electroluminescence element of this invention.

Figure 5D:
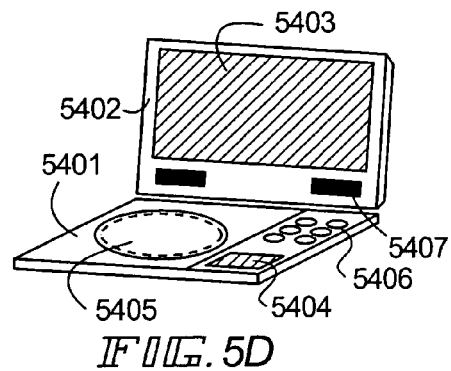

Shown in FIG. 5(D) is a mobile image reproducing apparatus having a recording medium (more specifically, a DVD reproducing apparatus) which includes a body 5401, a housing 5402, a display portion A 5403, a display portion B 5404, a recording medium (DVD, etc.) reading portion 5404, an operation key 5406, a speaker 5407, and the like. The display portion A 5403 mainly displays image information, while the display portion B 5404 mainly displays textual information. Each of the display portion A 5403 and the display portion B 5404 is manufactured by using the light emission device having the electroluminescence element of this invention. In addition, the image reproducing apparatus having a recording medium includes home-use game machines, or the like.

Figure 5E:
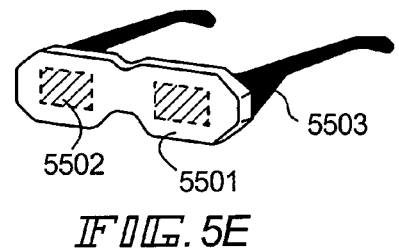

Shown in FIG. 5(E) is a goggle type display (head-mounted display) which includes a body 5501, a display portion 5502, and an arm 5503. The display portion 5502 is manufactured by using the light emission device having the electroluminescence element of this invention.

Figure 5F:
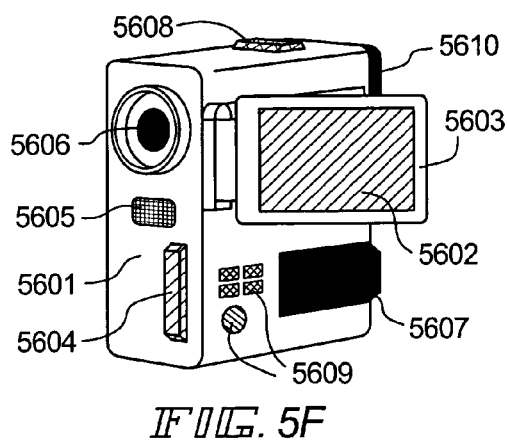

Shown in FIG. 5(F) is a video camera which includes a body 5601, a display portion 5602, a housing 5603, an external connection port 5604, a remote control receiving portion 5605, an image receiving portion 5606, a battery 5607, an audio input portion 5608, operation keys 5609, an eye piece 5610, and the like. The display portion 5602 is manufactured by using the light emission device having the electroluminescence element of this invention.

Figure 5G:
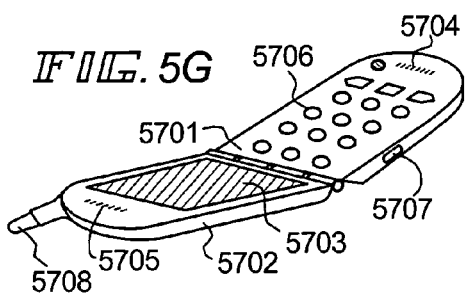

Shown in FIG. 5(G) is a mobile phone which includes a body 5701, a housing 5702, a display portion 5703, an audio input portion 5704, an audio output portion 5705, an operation key 5706, an external connection port 5707, an antenna 5708, and the like. The display portion 5703 is manufactured by using the light emission device having the electroluminescence element of this invention. In addition, it is possible to suppress power consumption of the mobile phone by displaying white characters on a black background on the display portion 5703.

As described in the foregoing, the range of application of the light emission device having the electroluminescence element of this invention is remarkably wide, and it is possible to apply this light emission device to electric appliances of various fields.

According to the present invention, it is possible to provide novel organometal complexes which is obtainable with good yield by using a ligand which can be easily synthesized. Particularly, it is possible to provide the novel organometal complexes which are excellent in heat resistance.

Also, it is possible to provide an electroluminescence element having high light emission efficiency by manufacturing the electroluminescence element using the organometal complex. Further, it is possible to provide a light emission device which is suppressed in power consumption by manufacturing the light emission device using the electroluminescence element.

What is claimed is:

1. A light emission material comprising:
an organometal complex having a structure represented by the general formula (1):

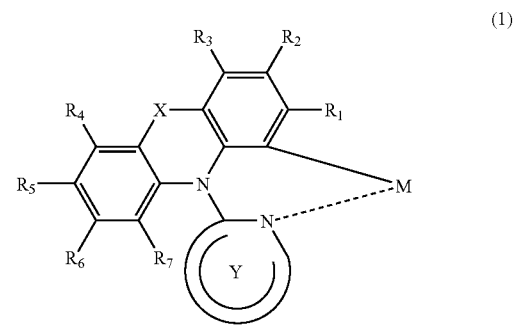

wherein R1 to R7 respectively represent any one of a hydrogen atom, a halogen atom, a lower alkyl group, an alkoxyl group, an acyl group, a nitro group, a cyano group, an amino group, a dialkylamino group, a diarylamino group, a vinyl group, an aryl group, or a heterocyclic residue;
wherein X represents an oxygen atom or a sulfur atom;
wherein Y represents a heterocyclic residue containing a nitrogen atom as a heteroatom; and
wherein M represents a group IX atom or a group X atom.

2. A light emission material comprising:
an organometal complex having a structure represented by the general formula (2):

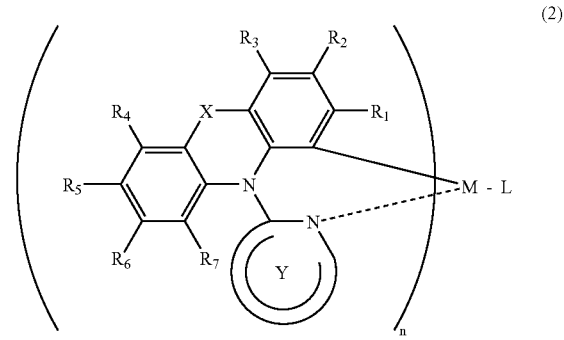

wherein R1 to R7 respectively represent any one of a hydrogen atom, a halogen atom, a lower alkyl group, an alkoxy group, an acyl group, a nitro group, a cyano group, an amino group, a dialkylamino group, a diarylamino group, a vinyl group, an aryl group, or a heterocyclic residue;
wherein X represents an oxygen atom or a sulfur atom;
wherein Y represents a heterocyclic residue containing a nitrogen atom as a heteroatom;

wherein M represents a group IX atom or a group X atom, and n=2 when the M is the group IX atom, while n=1 when the M is the group X atom; and wherein L represents any one of a monoanionic bidentate chelate ligand having a beta-diketone structure, a monoanionic bidentate chelate ligand having a carboxyl group, or a monoanionic bidentate chelate ligand having a phenolic hydroxyl group.

3. The light emission material according to claim 1, wherein the Y is a heterocyclic residue comprising a five-membered ring or a six-membered ring.

4. The light emission material according to claim 1, wherein the Y is a 2-pyridyl group.

5. A light emission material comprising:
an organometal complex having a structure represented by the general formula (3),

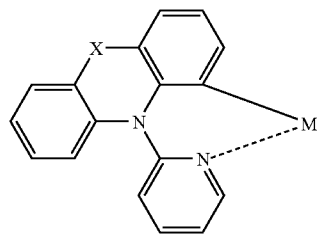

(3)

wherein X represents an oxygen atom or a sulfur atom; and
wherein M represents a group IX atom or a group X atom.

6. A light emission material comprising:
an organometal complex having a structure represented by the general formula (4):

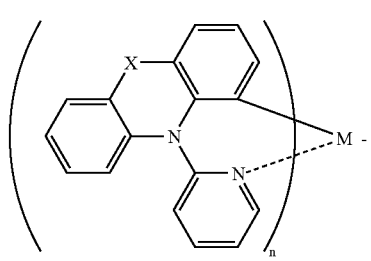

(4)

wherein X represents an oxygen atom or a sulfur atom;
wherein M represents a group IX atom or a group X atom, and n=2 when the M is the group IX atom, while n=1 when the M is the group X atom; and
wherein L represents any one of a monoanionic bidentate chelate ligand having a beta-diketone structure, a monoanionic bidentate chelate ligand having a carboxyl group, or a monoanionic bidentate chelate ligand having a phenolic hydroxyl group.

7. The light emission material according to claim 1, wherein the M is iridium or platinum.

8. The light emission material according to claim 2, wherein the M is iridium or platinum.

9. The light emission material according to claim 5, wherein the M is iridium or platinum.

10. The light emission material according to claim 6, wherein the M is iridium or platinum.

11. The light emission material according to claim 2, wherein the L is any one of monoanionic bidentate chelate ligands represented by the structural formulas (5) to (11)

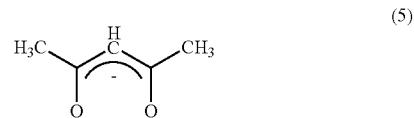

(5)

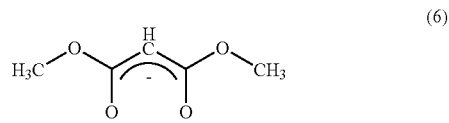

(6)

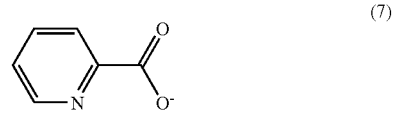

(7)

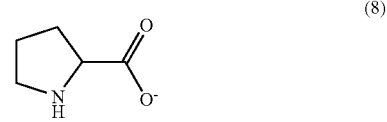

(8)

(9)

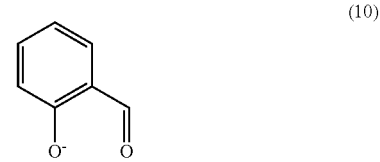

(10)

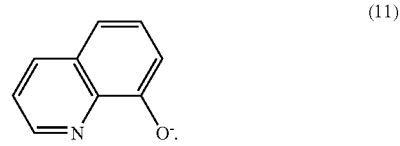

(11)

12. The light emission material according to claim 6, wherein the L is any one of monoanionic bidentate chelate ligands represented by the structural formulas (5) to (11)

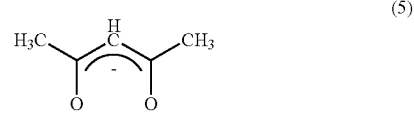

(5)

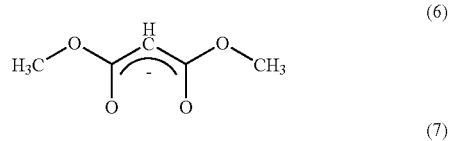

(6)

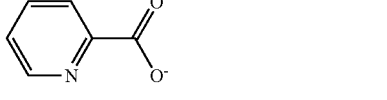

(7)

-continued

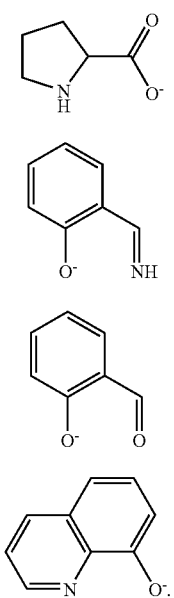

(8)

(9)

(10)

(11)

13. An electronic appliance comprising an electroluminescence element comprising the light emission material according to claim 1, wherein the electronic appliance is selected from the group consisting of a video camera, a digital camera, a goggle type display, a navigation system, an audio reproduction apparatus, a notebook type personal computer, a game machine, a personal digital assistant and an image reproduction apparatus having a recording medium.

14. A light emission material comprising:
an organometal complex having a structure represented by the general formula (1):

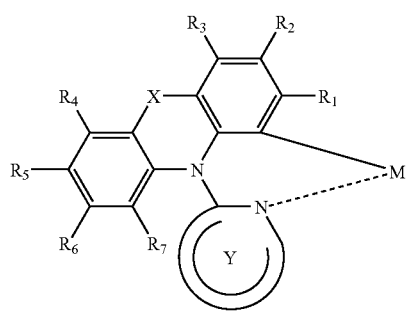

(1)

wherein each of pairs of R1 and R2, R2 and R3, R4 and R5, and R5 and R6 is combined into an aromatic ring;
wherein X represents an oxygen atom or a sulfur atom;
wherein Y represents a heterocyclic residue containing a nitrogen atom as a heteroatom; and
wherein M represents a group IX atom or a group X atom.

15. A light emission material comprising:
an organometal complex having a structure represented by the general formula (2):

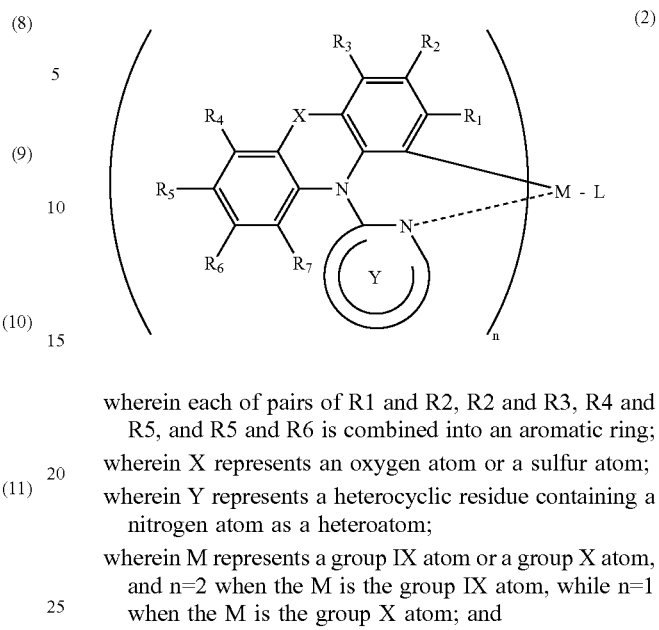

(2)

wherein each of pairs of R1 and R2, R2 and R3, R4 and R5, and R5 and R6 is combined into an aromatic ring;
wherein X represents an oxygen atom or a sulfur atom;
wherein Y represents a heterocyclic residue containing a nitrogen atom as a heteroatom;
wherein M represents a group IX atom or a group X atom, and n=2 when the M is the group IX atom, while n=1 when the M is the group X atom; and
wherein L represents any one of a monoanionic bidentate chelate ligand having a beta-diketone structure, a monoanionic bidentate chelate ligand having a carboxyl group, or a monoanionic bidentate chelate ligand having a phenolic hydroxyl group.

16. The light emission material according to claim 14,
wherein the Y is a heterocyclic residue comprising a five-membered ring or a six-membered ring.

17. The light emission material according to claim 14,
wherein the Y is a 2-pyridyl group.

18. The light emission material according to claim 14,
wherein the M is an iridium atom or a platinum atom.

19. The light emission material according to claim 15,
wherein the M is an iridium atom or a platinum atom.

20. The light emission material according to claim 15,
wherein the L is any one of monoanionic bidentate chelate ligands represented by the structural formulas (5) to (11)

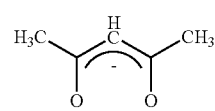

(5)

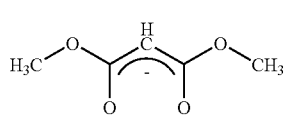

(6)

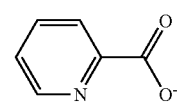

(7)

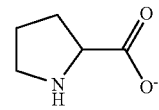

(8)

-continued

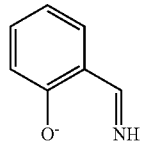 (9)

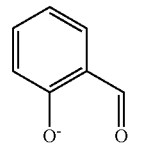 (10)

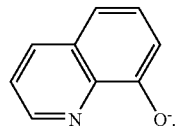 (11)

21. An electronic appliance comprising an electroluminescence element comprising the light emission material according to claim 14, wherein the electronic appliance is selected from the group consisting of a video camera, a digital camera, a goggle type display, a navigation system, an audio reproduction apparatus, a notebook type personal computer, a game machine, a personal digital assistant and an image reproduction apparatus having a recording medium.

22. The light emission material according to claim 2, wherein the Y is a heterocyclic residue comprising a five-membered ring or a six-membered ring.

23. The light emission material according to claim 2, wherein the Y is a 2-pyridyl group.

24. An electronic appliance comprising an electroluminescence element comprising the light emission material according to claim 2, wherein the electronic appliance is selected from the group consisting of a video camera, a digital camera, a goggle type display, a navigation system, an audio reproduction apparatus, a notebook type personal computer, a game machine, a personal digital assistant and an image reproduction apparatus having a recording medium.

25. An electronic appliance comprising an electroluminescence element comprising the light emission material according to claim 5, wherein the electronic appliance is selected from the group consisting of a video camera, a digital camera, a goggle type display, a navigation system, an audio reproduction apparatus, a notebook type personal computer, a game machine, a personal digital assistant and an image reproduction apparatus having a recording medium.

26. An electronic appliance comprising an electroluminescence element comprising the light emission material according to claim 6, wherein the electronic appliance is selected from the group consisting of a video camera, a digital camera, a goggle type display, a navigation system, an audio reproduction apparatus, a notebook type personal computer, a game machine, a personal digital assistant and an image reproduction apparatus having a recording medium.

27. The light emission material according to claim 15, wherein the Y is a heterocyclic residue comprising a five-membered ring or a six-membered ring.

28. The light emission material according to claim 15, wherein the Y is a 2-pyridyl group.

29. An electronic appliance comprising an electroluminescence element comprising the light emission material according to claim 15, wherein the electronic appliance is selected from the group consisting of a video camera, a digital camera, a goggle type display, a navigation system, an audio reproduction apparatus, a notebook type personal computer, a game machine, a personal digital assistant and an image reproduction apparatus having a recording medium.

* * * * *